United States Patent
Baerson et al.

(10) Patent No.: US 7,732,666 B1
(45) Date of Patent: Jun. 8, 2010

(54) O-METHYLTRANSFERASE GENE FROM SORGHUM CLONING, EXPRESSION, TRANSFORMATION AND CHARACTERIZATION

(75) Inventors: Scott R. Baerson, Oxford, MS (US); Agnes M. Rimando, Oxford, MS (US); Franck E. Dayan, Oxford, MS (US); Zhiqiang Pan, Oxford, MS (US); James J. Polashock, Hainesport, NJ (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 440 days.

(21) Appl. No.: 11/514,512

(22) Filed: Sep. 1, 2006

(51) Int. Cl.
*A01H 1/00* (2006.01)
*C07H 21/04* (2006.01)
*C07K 14/415* (2006.01)
*C12N 15/00* (2006.01)

(52) U.S. Cl. .......................... 800/295; 435/6; 435/468; 435/419; 435/320.1; 435/183; 530/370; 536/23.1; 536/23.6; 800/278

(58) Field of Classification Search .................. 435/6, 435/69.1, 468, 419, 252.3, 320.1, 183; 530/370; 536/23.2, 23.6; 800/278, 295
See application file for complete search history.

(56) References Cited

U.S. PATENT DOCUMENTS

2004/0214272 A1* 10/2004 La Rosa et al. ............ 435/69.1

OTHER PUBLICATIONS

Smith et al., GenBank Accession No. AF387790, Jan. 2, 2002, direct submission.*

* cited by examiner

*Primary Examiner*—Phuong T Bui
(74) *Attorney, Agent, or Firm*—John D. Fado; Evelyn M. Rabin

(57) ABSTRACT

This invention relates to an O-methyltransferase gene cloned from sorghum, the sorghum O-methyltransferase-3 gene, SbOMT3. Quantitative real-time RT-PCR and recombinant enzyme studies with putative O-methyltransferase sequences obtained from an EST data set from sorghum have led to the identification of the novel root hair-specific O-methyltransferase designated SbOMT3. Transgenic plants which express SbOMT3 can convert resveratrol into pterostilbene in planta. SbOMT3 is also involved in the biosynthesis of sorgoleone.

28 Claims, 11 Drawing Sheets

Fig. 4A

Fig. 7A
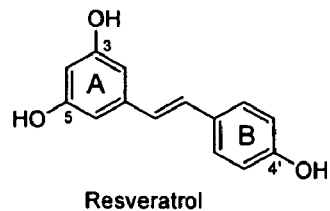
Resveratrol
Fig. 7B
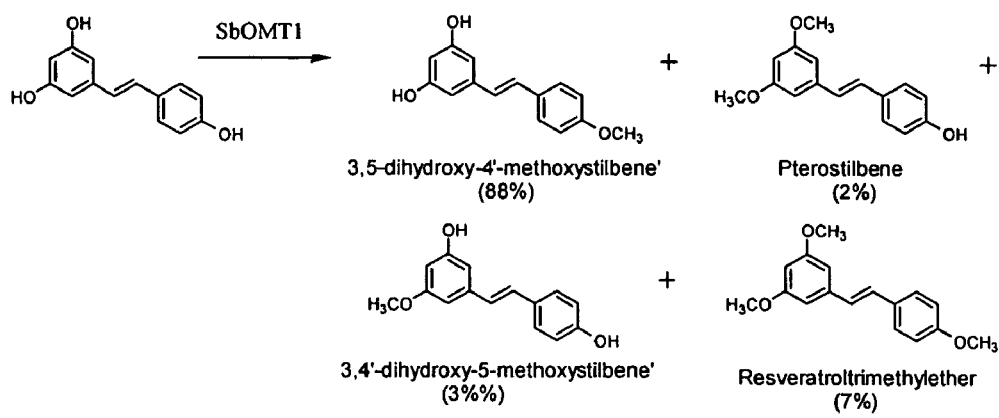
3,5-dihydroxy-4'-methoxystilbene' (88%) + Pterostilbene (2%) + 3,4'-dihydroxy-5-methoxystilbene' (3%%) + Resveratroltrimethylether (7%)
Fig. 7C
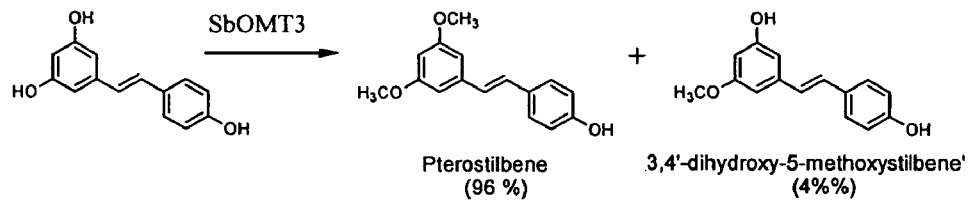
Pterostilbene (96 %) + 3,4'-dihydroxy-5-methoxystilbene' (4%%)
Fig. 7

O-METHYLTRANSFERASE GENE FROM SORGHUM CLONING, EXPRESSION, TRANSFORMATION AND CHARACTERIZATION

BACKGROUND OF THE INVENTION

1. Field of the Invention

This invention relates to an O-methyltransferase gene cloned from sorghum, the sorghum O-methyltransferase-3 gene, SbOMT3; a construct containing the gene and its promoter; a vector containing the gene; sorghum O-methyltransferase-3 protein, SbOMT3; a method of making SbOMT3 protein; a method of transforming plants; and transgenic plants which express SbOMT3 and thereby convert resveratrol into pterostilbene in planta.

2. Description of the Relevant Art

Resveratrol is a grape phytoalexin that protects plants against important plant pathogens such as *Botrytis cinerea* (Adrian et al. 1997. *J. Chem. Ecol.* 23: 1689-1702; Hoos and Blaich. 1990. *J. Phytopathol.* 129: 102-110). This metabolite is also beneficial to human health by acting as a strong antioxidant (Martinez and Moreno. 2000. *Biochem. Pharmacol.* 59: 865-870; Stivala et al. 2001. *J. Biol. Chem.* 276: 22586-22594) and by having cancer chemopreventive properties (Jang et al. 1997. *Science* 275: 218-220). Pterostilbene, a methylated analogue of resveratrol was demonstrated to have similar antioxidant and cancer chemopreventive properties as resveratrol (Rimando et al. 2002. *J. Agric. Food Chem.* 50: 3453-3457). Pterostilbene has been shown to have beneficial pharmaceutical and nutraceutical effects for humans and animals. It has been reported to be cytotoxic against a number of cancer cell lines including human breast cancer and murine lymphoid neoplasma cell lines (Rimando et al. 1994. *Nat. Prod. Lett.* 4: 267-272), and to lower blood glucose level in streptozidin-induced diabetic mice (Manickam et al. 1997. *J. Nat. Prod.* 60: 609-610). Pterostilbene is more fungitoxic than resveratrol against the plant pathogens *Botrytis cinerea*, *Cladosporium cucumerinum*, *Pellicularia sasakii*, *Piricularia oryzae*, and *Plasmopora viticola* (Langcake et al. 1979. *Phytochemistry* 18: 1025-1027). Pterostilbene also inhibited fungi involved in the chronic disease of grapevines, esca, (*Phaeoacremonium aleophilum*, *Phaeomoniella chlamydospora*, *Libertella blepharis*, *Fomitiporia punctata* and *Stereum hirsutum*), whereas resveratrol did not inhibit mycelial growth of these fungi (Mazzullo et al. 2000. *Phytopathol. Mediterr.* 39: 357-365). Furthermore, pterostilbene was inhibitory against the human pathogens *Candida albicans*, *Cryptococcus neoformans*, *Staphylococcus aureus*, and methicillin-resistant *S. aureus*, while resveratrol was ineffective against those disease agents (Rimando et al. 2003a. *Abstracts of Papers: 219th American Chemical Society National Meeting*: AGFD-081).

*Sorghum bicolor* (L.) Moench is one of the most important cereal crops worldwide (Doggett, H.1988. *Sorghum, $2^{nd}$ Edition*, Blackwell Publishing, Ames, Iowa), surpassed only by wheat, rice, corn and barley in total acreage, with the United States currently accounting for a major portion of total world production and exports (FAOSTAT data, faostat.fao.org; accessed March 2006). Allelopathy, the chemical inhibition of one plant species by another, represents a form of chemical warfare between neighboring plants competing for limited light, water, and nutrient resources (Inderjit and Duke. 2003. *Planta* 217: 529-539; Bais et al. 2004. *Trends Plant Sci.* 9: 26-32). The allelopathic properties of sorghum were first suggested from observations of reduced growth of other crop species when grown in rotation; moreover certain sorghum species such as Sudan grass (*Sorghum sudanese*) can produce largely weed-free monocultures without the use of synthetic herbicides (reviewed by Duke et al. 2005. *Outlooks Pest Management* 16: 64-68). Allelopathic interactions have been proposed to have profound effects on the evolution of plant communities through the loss of susceptible species via chemical interference, and by imposing selective pressure favoring individuals resistant to inhibition from a given allelochemical (e.g., Schulz and Wieland. 1999. *Chemoecology* 9: 133-141; Bais et al., supra). In addition, allelochemicals released by grain crop species such as barley, rye, and sorghum are thought to play a significant role in their efficacy as weed suppressants when used as cover crops or within intercropping systems (Duke et al. 2002. *J. Pestic. Sci.* 27: 298-306; Weston and Duke. 2003. *Crit. Rev. Plant Sci.* 22: 367-389).

Current evidence suggests that a family of allelochemicals active at micromolar concentrations, referred to as sorgoleones, may account for much of the allelopathic properties of *Sorghum* spp. (Netzly and Butler. 1986. *Crop Sci.* 26: 775-780; Einhellig and Souza. 1992. *J. Chem. Ecol.* 18: 1-11; Czarnota et al. 2001. *Weed Technol.* 15: 813-825). The term sorgoleone is most frequently used to describe the compound corresponding to the predominant congener identified in sorghum root exudates (Kagan et al. 2003. *J. Agric. Food Chem.* 51: 7589-7595), 2-hydroxy-5-methoxy-3-[(Z,Z)-8',11',14'-pentadecatriene]-p-benzoquinone (FIG. 1), which has been estimated to account for as much as 85% of the exudate material (w/w) in some varieties (Czarnota et al. 2001, supra). The remaining exudate largely consists of sorgoleone congeners differing in the length or degree of saturation of the aliphatic side chain, and in the substitution pattern of the quinone ring (Kagan et al., supra; Rimando et al. 2003. *J. Nat. Prod.* 66: 42-45). The fact that sorgoleone acts as a potent broad-spectrum inhibitor active against many agronomically important monocot and dicot weed species, exhibits a long half-life in soil, and appears to effect multiple targets in vivo (e.g., Netzly and Butler. 1986, supra; Einhellig and Souza, supra; Nimbal et al. 1996. *J. Agric. Food Chem.* 44: 1343-1347; Rimando et al. 1998. *J. Nat. Prod.* 61: 927-930; Czarnota et al. 2001, supra; Bertin et al. 2003 *Plant Soil* 256: 67-83; Duke, S. O. 2003. *Trends Biotechnol.* 21: 192-195) may make it promising for development as a natural product alternative to synthetic herbicides (Duke, supra).

Both pterostilbene and sorgoleone have important roles in food crops; namely, pterostilbene has been shown to have beneficial pharmaceutical and nutraceutical effects for humans and animals and the allelopathic interactions of sorgoleone can suppress the growth and effects of weeds. Thus, knowing the genetic determinants of pterostilbene biosynthesis and sorgoleone biosynthesis could provide a novel and powerful tool, for enrichment of pterostilbenes and sorgoleones in important food crops. Increasing pterostilbene content in staple crops such blueberries, cranberries, and grapes could help in the alleviation of high cholesterol levels in patients, a condition which affects a large percentage of the world's population. Furthermore, the SbOMT3 gene could be used to alter food plants to selectively modify pterostilbene content and/or composition to provide protection against certain other diseases such as cancer. Thus, the sorghum O-methyltransferase can be used to generate transgenic plants with enhanced levels of pterostilbene in species such as grapes and blueberries that produce resveratrol (Adrian et al. 2000. *J. Agric. Food Chem.* 48: 6103-6105; Pezet and Pont. 1988. *Plant Physiol. Biochem.* (*Paris*) 26: 603-607; Rimando et al. 2000. *Abstracts of Papers: 220th American Chemical Society National Meeting*: AGFD-074; Rimando and Barney. 2003*b*.

*Abstracts of Papers: The 3rd World Congress on Medicinal and Atomatic Plants for Human Welfare:* PP10-07) resulting in more disease resistant varieties that also have higher nutraceutical value. It is a primary object of this invention to provide a molecular tool and method for increasing accumulation of pterostilbenes in plant cells.

In addition to utilizing the SbOMT3 gene to generate increased levels of pterostilbenes in plants which already produce resveratrol, i.e., plants such as blueberries, grapes and cranberries, the SbOMT3 gene can be used in combination with a resveratrol synthase gene to produce pterostilbene in any plant species. The enzymatic production of resveratrol in plants requires only the presence of the ubiquitous substrates p-coumaryl-CoA and malonyl-CoA (Austin and Noel. 2003. *Nat. Prod. Rep.* 20: 79-110); therefore, a resveratrol synthase gene such as the stilbene synthase gene from *Arachis hypogaea* (peanut; Lanz et al. 1991. *J. Biol. Chem.* 15: 9971-9976) can be used to generate pterostilbene in planta. The resulting transgenic plants expressing both transgenes, i.e., O-methyltransferase (SbOMT3) and stilbene synthase, simultaneously, would exhibit increased resistance to pathogen infection and also produce fruit that has higher nutraceutical value. This strategy could also be deployed in species where resveratrol is in limiting quantities, to achieve higher accumulation levels of pterostilbene.

We have isolated SbOMT3, a novel O-methyltransferase gene from *Sorghum bicolor*. The recombinant enzyme, SbOMT3, has been shown in vitro and in vivo to use resveratrol as a substrate to produce pterostilbene.

SUMMARY OF THE INVENTION

We have cloned and expressed SbOMT3, an O-methyltransferase gene from sorghum, and confirmed that its expression results in the production of the enzyme sorghum O-methyltransferase-3 (SbOMT3) in vitro and in vivo.

In accordance with this discovery, it is an object of the invention to provide an isolated nucleic acid molecule which encodes the SbOMT3 protein, an enzyme involved in the regulation of conversion of resveratrol to pterostilbene.

It is a further object of the invention to provide a construct which encodes the *Sorghum bicolor* O-methyltransferase-3 protein.

It is a still further object of the invention to provide a vector which comprises a construct which is capable of expressing said O-methyltransferase gene.

It is an additional object of the invention to provide transgenic plants, plant cells, and seeds containing the nucleic acid construct.

It is a another object of the invention to provide a method of transforming the SbOMT3 gene into plants by administering a vector, wherein said vector comprises an effective amount of a nucleic acid construct, which is a DNA sequence capable of transforming the SbOMT3 gene into a plant, and whereby said administration of the vector is effective for inducing pterostilbene biosynthesis in said plant through conversion of the existing substrate resveratrol present in said plant.

It is a another object of the invention to provide a method of inducing pterostilbene biosynthesis in a plant by utilizing a two-gene strategy wherein the plant is transformed with a first gene capable of producing resveratrol in vivo from ubiquitously available precursors, said resveratrol thereby being available as a substrate for SbOMT3, said enzyme resulting from the in planta expression of a second gene, SbOMT3, and wherein expression of both genes results in the production of pterostilbene in said plant. Preferably, said first gene is the gene encoding stilbene synthase enzyme and said second gene is SbOMT3. Said plant can be a plant wherein the expression of both the stilbene synthase enzyme and SbOMT3 can generate resveratrol making it available to be converted into pterostilbene or the expression of both can increase the amount of resveratrol in plants already capable of producing resveratrol, thereby generating increased levels of pterostilbene in plants already capable of generating resveratrol and pterostilbene, but now capable of producing increased amounts.

It is yet another object of the invention to provide a method of manipulating pterostilbene content in plants by stably transforming a plant with an isolated nucleotide molecule capable of modulating pterostilbene content, operably linked with a promoter capable of driving expression of a gene in a plant cell.

Other objects and advantages of this invention will become readily apparent from the ensuing description.

BRIEF DESCRIPTION OF THE DRAWINGS

FIG. 2A shows sorgoleone levels determined by HPLC analysis of root exudates prepared from 5-day old etiolated seedlings of *S. bicolor*, genotypes BTx623 versus SX-17. Data are shown as mean±SD. Open bars represent total sorgoleone content (μg/g fw), and closed bars represent sorgoleone content as a percent of total exudates (w/w). FIG. 2B depicts GC-MS analysis performed on methanol extracts prepared from roots of 8-day old seedlings of *S. bicolor*, genotype BTX623. The graph represents the total ion chromatogram showing the peaks of 5-(8,11,14)-pentadecatrienyl resorcinol-3-methyl ether at 18.3 min and 5-(8,11,14)-pentadecatrienyl resorcinol at 21.8 min. FIG. 2C shows the extracted ion chromatogram defined at m/z 314 for 5-(8,11,14)-pentadecatrienyl resorcinol and m/z 328 for the 3-methyl ether derivative, with the corresponding mass spectra for the two peaks shown as insets.

FIG. 3A shows the relative expression levels of three OMT sequences in different *S. bicolor* tissues determined by quantitative real-time RT-PCR using gene-specific primers. Data were normalized to an internal control (18S rRNA), and the $\Delta\Delta C_T$ method was used to obtain the relative expression level for each sequence. Data are expressed as mean±SD. FIG. 3B shows the relative expression levels of two *S. bicolor* control genes: chlorophyll a/b-binding protein (CAB 2__9279) and a polyubiquitin-like sequence (UBI 2__9314).

FIG. 4 shows the sequence alignment and genomic organization of SbOMT1, SbOMT2, and SbOMT3. FIG. 4A shows the deduced amino acid sequences of SbOMT1, SbOMT2, and SbOMT3 were aligned with three related plant type I OMTs (*M. sativa* 1-7 OMT, He et al. 1998. *Plant Mol. Biol.* 36: 43-54; *R. hybrida* OOMT1, Lavid et al. 2002. *Plant Physiol.* 129: 1899-1907; Gang et al. 2002. *Plant Cell* 14: 505-519) using ClustalW. Residues important for catalysis, substrate binding, and S-Adenosyl-L-Methionine (SAM) binding are indicated based on OMT crystallography studies performed by Zubieta et al. (2001. *Nat. Struct. Biol.* 8: 271-279) and Zubieta et al. (2002. *Plant Cell* 14:1265-1277), and by computational homology modeling of SbOMT3. Identical and similar amino acids are shaded with black and gray, respectively.

FIG. 6A shows a ribbon diagram of the SbOMT3 monomer three-dimensional structure. Alpha helices are indicated in red, connecting loops in green, and beta strands in yellow. N- and C-termini are also shown. FIG. 6B shows a close-up view of the three-dimensional model of the SbOMT3 active site containing S-Adenosyl-L-Methionine (SAM) and a docked molecule of 5-(8,11,14)-pentadecatrienyl resorcinol. FIG. 6C shows close-up molecular surface views of the I-7-OMT and SbOMT3 active sites, with I-7-OMT shown complexed with the isoflavone daidzein.

FIGS. 7A-7C depict the structure of resveratrol (FIG. 7A) and products resulting as a consequence of methylation of resveratrol by SbOMT1 (FIG. 7B) and by SbOMT3 (FIG. 7C).

FIG. 10A shows the average pterostilbene content from two technical replicates; FIG. 10B depicts the real-time PCR analysis of 35S::SbOMT3 (OMT) and 35S:: stilbene synthase (RS) transcript levels from assays performed in triplicate. Values are shown as average±S.D.

DETAILED DESCRIPTION OF THE INVENTION

Figure 1:
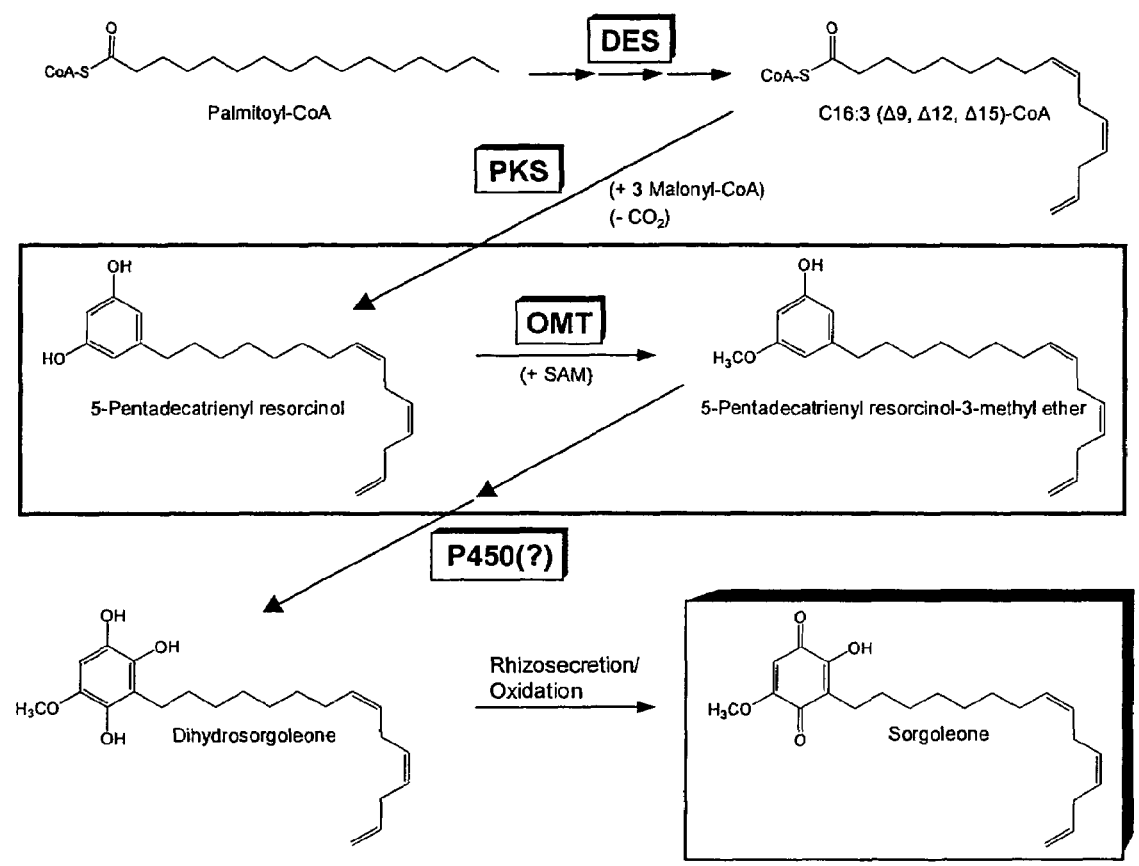
FIG. 1 depicts the proposed biosynthetic pathway for sorgoleone.

This invention concerns the cloning and functional analysis of an O-methyl-transferase gene cloned from sorghum, the sorghum O-methyltransferase-3 gene, SbOMT3. The SbOMT3 gene (SEQ ID NO:1) encodes the protein, sorghum O-methyl-transferase-3 (SbOMT3). SbOMT3 (SEQ ID NO:2) is capable of catalyzing the formation of both pterostilbene and sorgoleone. Using the compositions and methods of the invention, resveratrol can be converted to pterostilbene in planta. The resveratrol can be generated through the action of an in vivo-expressed stilbene synthase gene which is capable of producing resveratrol from common precursors in the plant. In addition, resveratrol can be native to the plant being transformed, i.e., resveratrol which is endogenously produced as for example in grapes, cranberries, and blueberries. Resveratrol, resulting from either circumstance, is an appropriate substrate for conversion to pterostilbene in planta through the action of in planta-expressed SbOMT3. The nucleic acid molecules, constructs and vectors of the invention and the methods of using them can be utilized to generate or increase pterostilbene in important food crops.

The identification and isolation of the SbOMT3 gene resulted from our strategy for isolating genes encoding enzymes involved in sorgoleone biosythesis. Sorgoleone biosynthesis likely occurs exclusively in root hairs, which appear as cytoplasmically dense cells in sorghum, containing large osmiophilic globules deposited between the plasmalemma and cell well, presumably associated with sorgoleone rhizosecretion (Czarnota et al. 2001, supra; Czarnota et al. 2003a. *J. Plant Sci.* 164: 861-866). Furthermore, the significant quantity of sorgoleone-containing exudates produced by these cells suggests that the corresponding mRNAs encoding these enzymes could be among the most abundant. Therefore, expressed sequence tag (EST) analysis was chosen as a gene isolation strategy to identify genes encoding enzymes involved in the biosynthesis of the allelochemical sorgoleone, as this approach is ideally suited for profiling the more abundant transcripts in a specific cell or tissue type (Ohlrogge and Benning. 2000. *Curr. Opin. Plant Biol.* 3: 224-228; Lange et al., 2000. *Proc. Natl. Acad. Sci. USA* 97: 2934-2939; Guterman et al., 2002. *Plant Cell* 10: 2325-2338; Fridman et al. 2005. *Plant Cell* 17: 1252-1267). The majority of the approximately 208,000 publicly-available *S. bicolor* ESTs (dbEST release 111105, Nov. 11, 2005, ncbi.nlm.nih.gov/dbEST) are derived from the genotype BTx623, a parental line commonly used in commercial breeding programs and also used for the development of detailed genetic maps (Menz et al. 2002. *Plant Mol. Biol.* 48: 483-499; Bowers et al. 2003. *Genetics* 165: 367-386). In addition, extensive sequence tagging of the *S. bicolor* genome by methylation filtration was recently performed using the isogenic, (CMS) paired inbred ATx623, providing an estimated 65% coverage for 96% of all genes (Bedell et al. 2005. *PLoS Biol.* 3, el 3). BTx623 was therefore initially selected as a model for the present work in order to utilize, as well as expand, the existing sorghum genomics infrastructure.

Labeling studies have demonstrated that the biosynthesis of sorgoleone involves the convergence of the fatty acid and polyketide pathways (Fate and Lynn. 1996. *J. Amer. Chem. Soc.* 118: 11369-11376; Dayan et al. 2003. *J. Biol. Chem.* 278: 28607-28611) through the action of a novel type III polyketide synthase activity utilizing fatty acyl-CoA starter units, resulting in the addition of a quinone head via iterative condensations of acetate extender units (FIG. 1; Cook et al., in preparation). Subsequent modifications of the alkylresorcinol intermediate are likely to be mediated by S-Adenosyl-L-Methionine (SAM)-dependent O-methyltransferases and dihydroxylated by P450 monooxygenases, yielding the reduced form of sorgoleone (dihydrosorgoleone). Upon exudation, the less stable hydroquinone rapidly oxidizes to the highly active benzoquinone form, which can persist in soil for extended periods (Netzly et al. 1988. *Weed Sci.* 36: 441-446; Einhellig and Souza, supra; Czarnota et al. 2001, supra).

The specific sequence of biosynthetic reactions leading to the formation of dihydrosorgoleone, starting from the 5-pentadecatrienyl resorcinol intermediate (FIG. 1) has not been previously determined. Moreover, despite the ecological and agronomic importance of this family of allelochemicals, a paucity of information exists concerning the enzymes participating in the sorgoleone biosynthetic pathway. In the present study, we have identified a 3-methyl ether derivative of the previously characterized 5-pentadecatrienyl resorcinol pathway intermediate by GC-MS analysis of sorghum root extracts, indicating that dihydroxylation of the resorcinol ring is preceded by O-methylation at the 3' position by a novel 5-n-alk(en)ylresorcinol-utilizing O-methyltransferase activity. To identify candidate O-methyltransferase sequences, as well as candidates representing other steps in the biosynthetic pathway, an annotated EST data set comprised of 5,469 quality 5' sequences was generated from a *S. bicolor* root hair-specific cDNA library. Follow-up real-time RT-PCR and recombinant enzyme studies with putative O-methyltransferase sequences obtained from this library have led to the characterization of three different cloned O-methyltransferase genes. Recombinant enzymes were produced and a root hair-specific O-methyltransferase which preferentially utilizes alkyresorcinolinic substrates proposed to be involved in the biosynthesis of sorgoleone was identified and designated SbOMT3.

Figure 8:
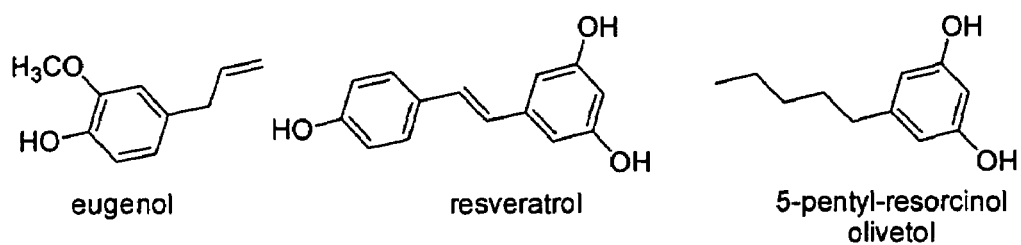
FIG. 8 shows a comparison of the specific activities of SbOMT1 and SbOMT3 on three different substrates: eugenol, resveratrol, and olivetol.
Figure 8:
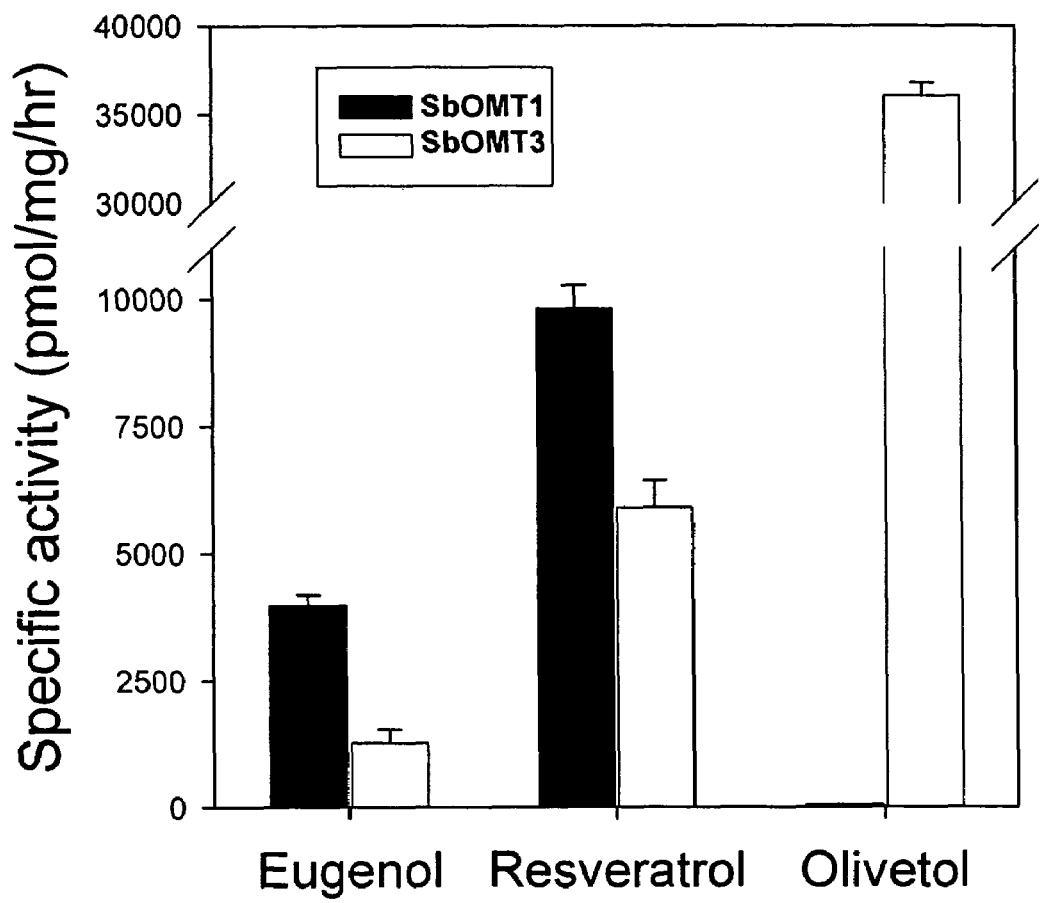

To determine the effect of SbOMT3 on pterostilbene biosynthesis, the three cloned O-methyltransferase genes were expressed and the recombinant enzymes were reacted with resveratrol (FIG. 7 and Example 9). The products from these reactions were then chemically analyzed by gas chromatography/mass spectroscopy to identify the products. The enzyme SbOMT1 reacted with resveratrol; however, resveratrol was not methylated in the correct position to produce pterostilbene. Thus, only about 2% of the product obtained was pterostilbene; 88% was 3,5-dihydroxy-4'-methoxystilbene. SbOMT2 did not react with resveratrol at all. SbOMT3 is an efficient generator of pterostilbene; 96% of the product obtained from the reaction of SbOMT3 and resveratrol is pterostilbene. Further, enzyme kinetic data indicate that both SbOMT1 and SbOMT3 use resveratrol as a substrate. However, only SbOMT3 methylates resveratrol in the correct position to produce pterostilbene to any significant extent (FIG. 8 and Table 1).

Based on the ability of O-methyltransferase SbOMT3 to generate pterostilbene from resveratrol in vitro via SAM-dependant methylation, a two-gene strategy was devised for the production of pterostilbene in transgenic plants. The strategy design comprised providing a first gene capable of producing resveratrol in vivo from ubiquitously available precursors. The resultant in vivo-generated resveratrol is then available to serve as a substrate for the protein encoded by the second gene, SbOMT3. Action of the expressed SbOMT3 yields pterostilbene. Stilbene synthase from the peanut plant (*Arachis hypogaea*) represents one enzyme capable of producing resveratrol from the common precursors coumaryl-CoA and malony-CoA (Schroder et al. 1988. *Eur. J. Biochem.* 172: 161-169). Related enzymes have also been characterized from other plant sources capable of synthesizing resveratrol, such as the grapevine (*Vitis vinifera*) resveratrol synthase (e.g., Becker et al. 2003. *FEMS Yeast Res.* 4: 79-85). Thus, the two-gene strategy for pterostilbene production is not reliant on a specific resveratrol/stilbene synthase enzyme in principle.

To test this strategy in planta, a binary vector was developed to simultaneously express both the peanut stilbene synthase enzyme and SbOMT3. The resulting construct, designated pCRO1, contains the two expression cassettes arranged in a head-to-tail orientation (See Example 13). To generate transgenic plants simultaneously expressing the peanut stilbene synthase and sorghum O-methyltransferase SbOMT3 enzymes, recombinant *A. tumefaciens* strains harboring pCRO1 were co-cultivated with leaf disk explants derived from *Nicotiana tabacum* (cv. Wisconsin 38). Transgenic tobacco plants were generated under kanamycin and carbenicillin selection.

To confirm the expression of both the peanut stilbene synthase and O-methyltransferase SbOMT3 expression cassettes in the various transgenic tobacco lines generated, quantitative real-time PCR analyses were performed using leaf tissues samples as previously described (Baerson et al., supra). To assess whether pterostilbene was produced in plants harboring pCRO1, leaf samples were collected from various transgenic tobacco lines and analyzed by gas chromatography/mass spectrometry (GC-MS) as previously described (Rimando et al. 2004. *J Agric Food Chem.* 52:4713-4719).

Transgenic plants expressing both a stilbene synthase-type enzyme in conjunction with the sorghum O-methyltransferase SbOMT3 accumulate the predicted product pterostilbene. A total of twelve independent tobacco lines transformed with the pCRO1 dual-cassette binary vector were screened for the expression of both the 35S::stilbene synthase and 35S::SbOMT3 transcripts, as well as for the presence of pterostilbene. Five out of the twelve lines were found to express the transgenes and all five expressed both the 35S:: stilbene synthase and 35S::SbOMT3 transcripts.

Significant amounts of pterostilbene, e.g., approximately 280 and 400 ng/gm dry weight, were detected.

Thus, expression of SbOMT3 together with the synthase gene can lead to production of pterostilbene in cells and plants where no endogenous resveratrol is present. However, additionally, the SbOMT3 gene can also be expressed in plants such as cranberry, grape, and blueberry, which endogenously produce resveratrol. In such plants, enhanced amounts of pterostilbene, over and above endogenous levels, could be generated.

The ability of SbOMT3 to efficiently use resveratrol as a substrate in planta is a central feature of this technology. The present proof-of-concept represents a relatively simple test case, which can be further optimized for the production of pterostilbene at higher levels or in specific tissues, for example, by the use of alternative promoter elements or other genetic elements required for the optimal expression of the transgene cassettes employed. It is anticipated that these relatively straight-forward modifications would result in significant increases in pterostilbene production, or in the production in specific plant organs such as developing seeds or fruits. In addition, alternative stilbene synthase enzymes could also be employed with more favorable kinetic properties, and pterostilbene production could thus be significantly enhanced.

In addition, while both transgene cassettes in pCRO1 use the strong, constitutively-expressed Cauliflower Mosaic Virus 35S (CaMV 35S) promoter (Odell et al. 1985. *Nature* 313: 810-812, gene promoters specifically induced by chemicals, pathogen infection, and other types of elicitors could be employed. In this case, pterostilbene would only be produced when crops are treated with specific chemical elicitors by growers, or automatically produced when plants are under attack by microorganisms or other adverse circumstances where pterostilbene production would be beneficial to overall crop yields.

The generation of sorgoleones is complex and involves multiple intermediary steps; however, as more information becomes available and the remaining biosynthetic enzymes become identified, SbOMT3 may additionally be used to increase the accumulation of sorgoleones in the root hairs and roots of sorghum and other food crops to ensure the suppression of weeds and thus higher yields of food crops.

The terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the SbOMT3 enzyme, operably linked to a promoter and/or other regulatory sequences.

As used herein, the term "express" or "expression" is defined to mean transcription alone. The regulatory elements are operably linked to the coding sequence of the SbOMT3 gene such that the regulatory element is capable of controlling expression of SbOMT3 gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence which specifically induces the SbOMT3 gene expression in root hairs and roots. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

As used herein, the term "expressed sequence tag" (EST) refers to a short strand of DNA (approximately 200 base pairs long) which is part of a cDNA. ESTs provide an indication of the abundance of the genes that are being expressed in that tissue at that stage of development. Because an EST is usually unique to a particular cDNA, and because cDNAs correspond to a particular gene in the genome, ESTs can be used to help identify unknown genes and to map their position in the genome.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. 1987. Meth. Enzymol. 143:277) and particle-accelerated or "gene gun" transformation technology (Klein et al. 1987. Nature (London) 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. Cloning Vectors: A Laboratory Manual; Weissbach and Weissbach. 1989. Methods for Plant Molecular Biology, Academic Press, New York; and Flevin et al. 1990. Plant Molecular Biology Manual, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to the SbOMT3 polypeptide that is substantially free of other proteins, lipids, carbohydrates or other materials with which it is naturally associated. One skilled in the art can purify SbOMT3 using standard techniques for protein purification. The purity of the SbOMT3 polypeptide can also be determined by amino-terminal amino acid sequence analysis.

The invention includes functional SbOMT3 polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of SbOMT3 polypeptide", refers to all fragments of SbOMT3 that retain SbOMT3 activity and function in the pterostilbene and sorgoleone biosynthetic pathway. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of SbOMT3 in the sorgoleone and/or pterostilbene accumulation pathway can be utilized in bioassays to identify functional fragments of SbOMT3 polypeptide or related polypeptides.

Modifications of the SbOMT3 primary amino acid sequence may result in further mutant or variant proteins having substantially equivalent activity to the SbOMT3 polypeptides described herein. Such modifications may be deliberate, as by site-directed mutagenesis, or may occur by spontaneous changes in amino acid sequences where these changes produce modified polypeptides having substantially equivalent activity to the SbOMT3 polypeptides. Any polypeptides produced by minor modifications of the SbOMT3 primary amino acid sequence are included herein as long as the biological activity of SbOMT3 is present; e.g., having a role in pathways leading to sorgoleone and pterostilbene accumulation in plants and in vitro.

A heterologous coding sequence refers to coding sequences which encode peptides or proteins, unrelated to, or, other than, the SbOMT3 polypeptides provided above and which are not intrinsically found in the position provided in the chimeric gene construct.

Genes encoding a SbOMT3 protein can be cloned using a variety of techniques according to the invention. The simplest procedure for the cloning of SbOMT3 genes requires the cloning of genomic DNA from an organism identified as producing an SbOMT3 protein, and the transfer of the cloned DNA on a suitable plasmid or vector to a host organism which does not produce the SbOMT3 protein, followed by the identification of transformed hosts to which the ability to produce the SbOMT3 protein has been conferred. The transforming SbOMT3-conferring DNA can be cleaved into smaller fragments and the smallest which maintains the SbOMT3-conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al.: supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a SbOMT3 polypeptide and which hybridize under stringent conditions, as described herein, to the SbOMT3 sequences disclosed herein, or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. For example, that portion of the SbOMT3 protein beginning with amino acid 209, i.e., isoleucine, and consisting of 94 contiguous amino acids or less (as described above), can be used to identify or isolate the SbOMT3 gene encoding said SbOMT3 protein in nucleotide sequences of plants other than sorghum. Thus, such a portion represents a "substantial portion" and can be used to establish "substantial identity", i.e., sequence identity of at least 80%, compared to the reference sequence, sorghum. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of one of the SbOMT3 polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, SbOMT3 activity as described herein. Such variants may result from, for example, genetic polymorphism or from human manipulation. Biologically active variants of a native SbOMT3 protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired SbOMT3 activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of SbOMT3 protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful cloning of SbOMT3 is a major technological advancement in our ability to engineer pterostilbene accumulation in plants. Deciphering the mechanism by which this gene functions to result in the mass accumulation of pterostilbene will aid in devising new strategies and/or control points for improving or introducing pterostilbene content in crops. The generation of sorgoleones is complex and involves many intermediaries, which are not as yet defined; however, SbOMT3 may likewise be used to increase the accumulation of sorgoleones in the root hairs and roots of sorghum and other food crops, the resultant allelopathic properties thus making possible higher yields of food crops.

EXAMPLES

Having now generally described this invention, the same will be better understood by reference to certain specific examples, which are included herein only to further illustrate the invention and are not intended to limit the scope of the invention as defined by the claims.

Example 1

Plant Materials and Growth Conditions

Seeds of S. bicolor genotype BTx623 were purchased from Crosbyton Seed Company (Crosbyton, Tex.), and SX-17 sorghum-Sudangrass hybrid seeds (S. bicolor x sudanense) were purchased from Dekalb Genetics (Dekalb, Ill.). SX-17 was used for sorgoleone content comparisons with BTx623; all other experiments described in this work involved only BTx623. Root tissues used for sorgoleone content determinations, analysis of C15:3 resorcinols, root hair preparations, and whole root systems used for real-time RT-PCR experiments were obtained from 5 or 8-day-old dark-grown seedlings grown under soil-free conditions using a capillary mat system devised by Czarnota and co-workers (Czarnota et al. 2001, supra). Immature leaves and shoot apices used for real-time RT-PCR experiments were isolated from seedlings maintained in a growth chamber at 28° C. for 8 days in standard (approximately 20×40 cm) nursery flats using Premier Pro Mix PGX potting media (Hummert International, Earth City, Mo.) under a combination of cool-white fluorescent and incandescent lighting at an intensity of approximately 400 µmol m$^{-2}$ s$^{-1}$ and a 16-h photoperiod. Developing panicles, mature leaves, and culm (stem) tissues used for real-time RT-PCR experiments were isolated from 10-week-old greenhouse-grown plants. At the time of harvest, panicles were partially exerted from flag leaf sheaths, just prior to anthesis. All harvested plant material was directly flash-frozen in liquid nitrogen and stored at ±80° C. prior to analysis, with the exception of material used for sorgoleone content determinations which involved fresh tissue extractions.

Example 2

Sorgoleone Content Determinations

Root systems from 5-day-old seedlings were weighed, immersed in chloroform and agitated for 30 seconds, then extracts were filtered through Whatman No. 1 filter discs (Whatman Inc., Florham Park, N.J.) to remove debris, concentrated in vacuo at 30° C. using a rotary evaporator (Buchi Rotovapor, Brinkmann Instruments, Westbury, N.Y.), then dried to completion under nitrogen gas, and weighed using an analytical balance. Dried extracts were then re-dissolved in acetonitrile (1.0 mg sample per mL of acetonitrile) and analyzed by high performance liquid chromatography (HPLC) using a Hewlett-Packard 1050 HPLC System (Agilent Technologies, Palo Alto, Calif.) equipped with an Alltech EPS C18 column (100 A, 3 µm, 150 mm length, 4.5 mm internal diameter; Alltech Associates Inc., Deerfield, Ill.). The sample was eluted as follows (solvent A is 2.5% acetic acid in water, solvent B is acetonitrile): 0-15 min 45% A/55% β isocratic; 15-22 min linear gradient from 55% to 100% B; 22-25 min 100% B; 25-26 min 100% to 55% B; 26-30 min 45% A/55% β isocratic. A flow rate of 2 mL/min was used and the sample injection volume was 20 µL. The peak corresponding to sorgoleone was monitored at 280 nm. Quantitation was based on a calibration curve using purified sorgoleone as an external standard.

To first assess the suitability of genotype BTx623 as a model, sorgoleone levels were determined by HPLC analysis of root exudates collected from 5-day-old, etiolated seedlings (see Methods). For comparison, an identical analysis was also performed with SX-17 seedlings, a previously characterized S. bicolor x S. sudanense hybrid (Czarnota et al. 2001, supra; Czarnota et al. 2003b. J. Chem. Ecol. 29: 2073-2083; Rimando et al., 2005. In: Semiochemicals in Pest and Weed Control, ACS Symposium Series 906, Petroski et al, eds., pp 59-70). The results of this comparison are shown in FIG. 2A. The total sorgoleone content of approximately 1500 µg/g fw measured in SX17 seedlings was in agreement with previously reported levels for this genotype (Czarnota et al. 2003b, supra; Rimando et al. 2005, supra), and were approximately 30% higher than those observed for BTx623 seedlings (FIG. 2A). Significant variation in sorgoleone content among different sorghum accessions is typically observed (Nimbal et al., supra; Czarnota et al. 2003b, supra), nevertheless the results obtained in the present study clearly indicate that the sorgoleone content of genotype BTx623 is comparable to levels observed in other accessions. Also of interest is the observation that the predominant sorgoleone congener, 2-hydroxy-5-methoxy-3-[(Z,Z)-8',11',14'-pentadecatriene]-p-benzoquinone (FIG. 1), represents a major constituent (41%-w/w) of the exudate material produced by BTx623 seedlings (FIG. 2A). Taken together, the data clearly demonstrate the suitability of the genotype BTx623 as a model system for identifying genes associated with the biosynthesis of sorgoleone.

Example 3

GC-MS Analysis of C15:3 Resorcinols

Root systems from 8-day-old seedlings were first immersed in chloroform with agitation for 30 seconds to remove sorgoleone, then lyophilized. Lyophilized material was pulverized using a mortar and pestle, followed by homogenization in methanol (approximately 10 g per 50 mL) for 1 min at 25,000 rpm. Homogenates were then filtered through Whatman No. 1 filter discs, then evaporated using a rotary evaporator (Büchi Rotovapor, Brinkmann Instruments, Westbury, N.Y.) at 30° C. Residues were then re-dissolved in methanol and transferred to GC vials. GC-MS analysis was performed using a JEOL GCMate II System (JEOL USA Inc., Peabody, Mass.) using a J&W DB-5 capillary column (0.25 mm internal diameter, 0.25 µm film thickness, 30 m length; Agilent Technologies, Forster City, Calif.). The GC temperature program was initially set to 110° C., raised to 300° C. at a rate of 6° C./min, then held at this temperature for 2.3 min.

Ultra high purity helium was used as carrier at a flow rate of 1.0 mL/min. The inlet (splitless), GC interface, and ion chamber temperatures were 250, 250, and 230° C., respectively. The sample injection volume used was 2.0 µL.

The mass spectrum of the peak at 21.8 (FIGS. 2B-C) showed fragment ions m/z 313 [M$^+$–H], 269 [313$^+$-CH=CH$_2$, —OH], 255 [269$^+$-CH$_2$], 241 [255$^+$-CH$_2$], 227 [241$^+$-CH$_2$], 213 [227$^+$-CH$_2$], 199 [213$^+$-CH$_2$], 185 [313$^+$-CH(CH$_2$CH=CH)$_2$H, -2OH], 171 [185$^+$-CH$_2$], 159 [314$^+$-(CH$_2$CH=CH)$_3$H, -2OH], 143 [314$^+$-(CH$_2$)$_2$(CH$_2$CH=CH)$_3$H, -2H$_2$O], 131 [159$^+$-2CH$_2$], 129 [143$^+$-CH$_2$], and 117 [131$^+$-CH$_2$] supporting the identification of the 5-(8,11,14)-pentadecatrienyl resorcinol intermediate. Similarly, the mass spectrum of the peak at 18.3 min (FIG. 2C) showed fragment ions m/z 328 [M$^+$], 285 [M$^+$+H—CH=CH$_2$, —OH], 269 [M$^+$-CH$_2$CH=CH$_2$, —H2O], 243 [269$^+$-CH=CH], 229 [243$^+$-CH$_2$], 201 [M$^+$+2H—(CH$_2$CH=CH)$_2$H, —OH, —OCH$_3$], 187 [201$^+$-CH$_2$], 171 [M$^+$-H, —(CH=CHCH$_2$)$_2$CH=CH$_2$, —H$_2$O, —OCH$_3$], 159 [M$^+$-(CH$_2$CH=CH)$_3$H, —OH, —OCH$_3$], 145 [159$^+$-CH$_2$], 132 [145$^+$-CH], 129 [171$^+$-(CH$_2$)$_3$], and 117 [159$^+$-(CH$_2$)$_3$], supporting the identification of the 5-(8,11,14)-pentadecatrienyl resorcinol-3-methyl ether intermediate.

Figure 2:
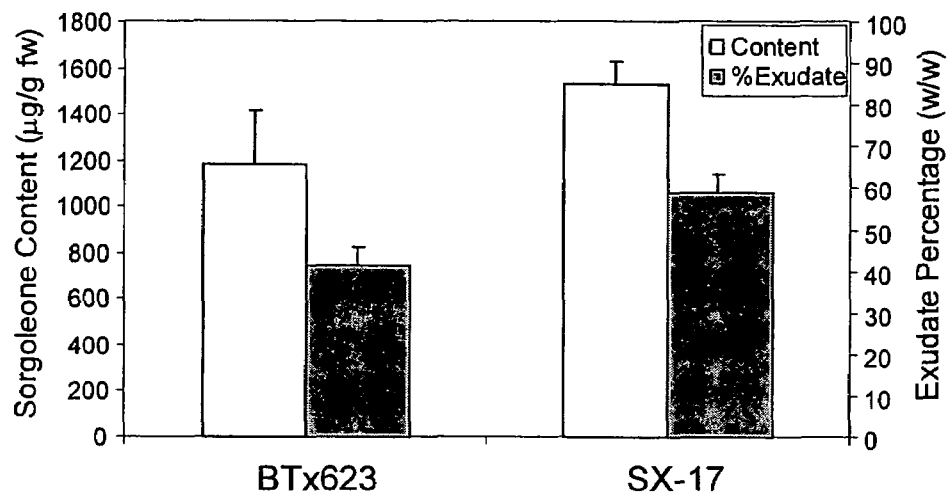
FIGS. 2A-2C show a comparison of sorgoleone production in BTx623 versus SX-17 and identification of sorgoleone biosynthetic pathway intermediates.
Figure 2:
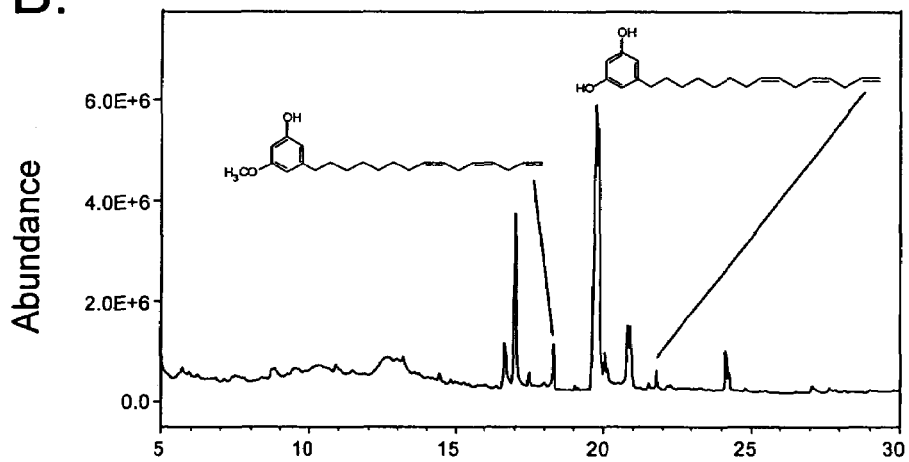
Figure 2:
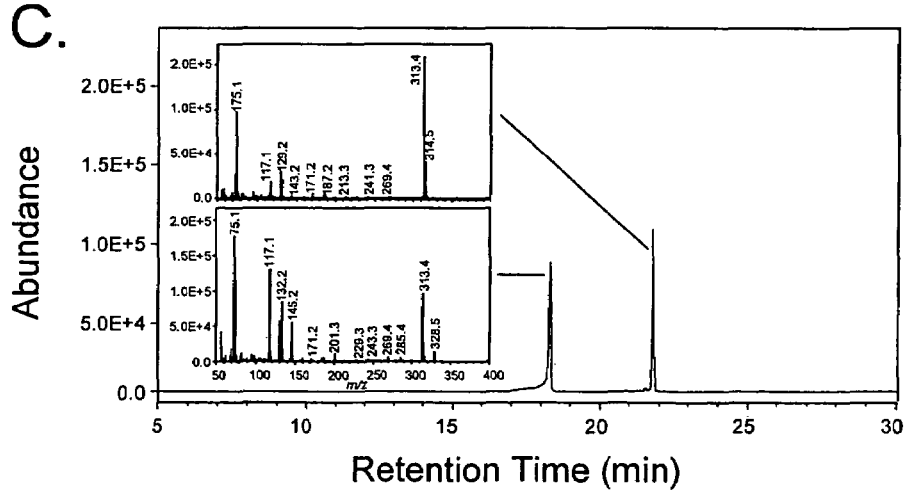

Collectively, these data support the pathway model proposed in FIG. 1, where dihydroxylation of the resorcinol ring is preceded by 3' O-methylation, likely catalyzed by a novel type I S-adenosyl-L-methionine-dependent O-methyltransferase (OMT) (Noel et al. 2003. *Recent Adv. Phytochem.* 37: 37-58) utilizing 5-[(8'Z,11'Z)-8',11',14'-pentadecatriene]resorcinol as a substrate in vivo.

Example 4 cDNA Library Construction

To create an EST data set useful for the identification of candidate O-methyl-transferases (OMT), fatty acid desaturase (DES), polyketide synthase (PKS), and cytochrome P450 (P450) sequences potentially encoding enzymes involved in sorgoleone biosynthesis, a directional cDNA library was constructed using the Uni-Zap XR vector. Root hairs were isolated from dark-grown 8-day-old BTX623 seedling root systems using the method devised by Bucher et al. (1997. *Plant Mol. Biol.* 35: 497-508), involving immersion in liquid nitrogen with gentle stirring, followed by filtration through a 250 µM aluminum mesh to remove root system debris. Purity of the root hair preparations was assessed by bright-field microscopy, and only highly enriched preparations were retained for subsequent cDNA library construction. Root hair preparations were stored at ±80° C. prior to RNA extraction. Total RNAs were isolated from root hairs using the Trizol reagent (Invitrogen Corporation, Carlsbad, Calif.) per manufacturer's instructions, with an additional homogenization step of 30 s at 25,000 rpm using a hand-held homogenizer. RNA purity was determined spectrophotometrically, and integrity was assessed by agarose gel electrophoresis. Poly-A+ mRNA was prepared from root hair total RNA using an Oligotex mRNA Midi Kit (Qiagen, Valencia, Calif.), and approximately 1.5 µg was used for construction of a directional cDNA library with the Uni-Zap XR cDNA library construction kit (Stratagene, La Jolla, Calif.), per manufacturer's instructions. A primary library of approximately 3×10$^6$ plaque forming units was obtained. To obtain an estimate of average insert size, 36 randomly-selected plaques from a primary library plating were sampled from NZY media (1.0% Casein digest (NZ amine), 0.5% NaCl, 0.5% yeast extract, 1.5% agar) plates using a sterile 1.0 ml pipet tip, then transferred into culture tubes containing 1.0 mL SM buffer (0.1 M NaCl, 1 mM MgSO$_4$, 0.2 M Tris (pH 7.5), 0.01% gelatin), and allowed to elute overnight at 4° C. with shaking. Phage eluates (2.5 µL) were then used as templates in 50 µL PCR reactions containing T3 and T7-specific PCR primers (Stratagene) using an Expand High Fidelity PCR kit (Roche Diagnostics Corporation, Indianapolis, Ind.) per manufacturer's instructions. After an initial denaturation step of 94° C. for 5 min, a thermal profile of 94° C. for 30 s, then 48° C. for 1 min 30 s, followed by 72° C. for 2 min for 35 cycles was used, and aliquots of the reactions were subsequently analyzed by agarose gel electrophoresis. By this analysis, the average insert size was estimated to be approximately 0.93 kb, ranging between 2.4 and 0.2 kb.

Example 5

EST Sequencing and Data Analysis

Recombinant plasmid-bearing colonies were obtained from the non-amplified *S. bicolor* root hair phagemid library by mass excision, then plasmid mini-preparations were performed for 6,624 randomly-selected isolates arrayed into 69 96-well plates. 5' DNA sequencing reactions were performed using ABI BigDye Terminator Cycle Sequence Ready Reaction kits (versions 2 and 3; Applied Biosystems, Foster City, Calif.) as previously described (Pratt et al. 2005. *Plant Physiol.* 139: 869-884). Base calling on raw sequence trace data was performed using PHRED software (Ewing et al. 1998. *Genome Res.* 8: 175-185), and vector, adapter, and low-quality sequence ends were filtered using an in-house processing script (C. Liang, F. Sun, H. Wang, J. Qu, R. M. Freeman Jr., L. H. Pratt, and M.-M. Cordonnier-Pratt, unpublished data), resulting in 5,469 high-quality sequences, or an 82.6% success rate. Provisional functional categorization of the assembled data set was performed by BLASTX analysis against *A. thaliana* peptide sequences downloaded from TIGR (AtGI release 12.1; tigr.org). An E value cutoff of E<10$^{-10}$ was applied to the parsed BLASTX returns, resulting in 1,972 significant matches obtained from the 3,128 queries performed (63%). TAIR locus identifiers from each match were then used to retrieve top-level functional categories from the Munich Information Center for Protein Sequences FunCatDB (Ruepp et al. 2004. *Nucleic Acids Res.* 32: 5539-5545). Gene discovery rate estimates were performed on EST clustering values generated as a function of the number of quality 5' sequences obtained following vector, adapter, and low-quality sequence removal using the discovery rate module within the MAGIC Gene Discovery software (Pratt et al. 2004. *Plant Physiol.* 139: 869-884). Provisional annotation of the data set was performed using the highest-scoring pairs obtained from the PIR-NREF database (Altscul et al. 1997. *Nucleic Acids Res.* 25: 3389-3402; Wu et al. 2002. *Nucleic Acids Res.* 30: 35-37), and the MAGIC Gene Discovery software package was implemented to facilitate subsequent data mining and contig analysis (Pratt et al., supra). To estimate the number of unique sequences expressed under the experimental conditions employed, a double-reciprocal plot was also generated for the number of unique sequences identified by cluster analysis versus the number of quality 5' sequences obtained, which provided a broad estimation of approximately 5,300 for the transcriptome size of root hair cells.

A striking number of the most highly expressed sequences in the root hair data set encode proteins potentially involved in pathogen defense, and/or detoxification processes associated with pathogen defense responses. For example, transcripts encoding enzymes such as peroxidases, catalases, glutathione-S-adenosyl transferases, phenylalanine ammonia-lyases, β-glucosidases, germins (oxalate oxidase), and pathogenesis-related proteins, are frequently upregulated in response to pathogen challenge in aerial plant tissues (e.g., Schenk at al. 2000. *Proc. Natl. Acad. Sci. USA* 97: 11655-11660; Ramonell et al. 2002. *Curr. Opin. Plant. Biol.* 5: 291-294), and also represent a significant portion of the most highly expressed genes in the root hair EST data set. Root hairs constitute up to 77% of the total surface area of root systems in cultivated crop species, representing the major interface between plants and soil-borne microflora (Parker et al. 2000. *Plant Cell* 12: 1961-1974; Walker et al. 2003. *Plant Physiol.* 132: 44-51), thus a major defensive role would be anticipated for root hairs, as well as other cell types in direct contact with the soil medium.

A second major group observed among the highly-expressed sequences potentially encode enzymes directly involved in sorgoleone biosynthesis, and in the biosynthesis of enzyme cofactors and fatty acid precursors required for the sorgoleone biosynthetic pathway. Putative DESs are included in this group, as well as proteins such as acetyl-CoA acyltransferase, acyl carrier protein, and acyl-CoA-binding protein, a ubiquitous family of 10 kD proteins found in eukaryotic organisms involved in the storage and intracellular transport of acyl-CoAs (Gossett et al. 1997. *Lipids* 31: 895-918). In addition, this second group includes several putative O-methyltransferases (OMTs), as well as enzymes such as S-adenosylmethionine synthetase (AdoMet synthetase) and methionine synthase, involved in the biosynthesis of the cofactor S-adenosylmethionine which serves as a methyl donor in OMT-catalyzed reactions (Joshi et al. 1998. *Plant Mol. Biol.* 37: 663-674; Noel et al., supra). Importantly, P450 and PKS-like sequences, as well as many additional putative DESS and OMTs were also identified within the EST data set, thus all of the major enzyme classes predicted to be required for the biosynthesis of sorgoleone appear to be highly represented (not shown).

BLAST queries performed using functionally characterized plant OMT peptide sequences against the *S. bicolor* root hair ESTs translated in all possible reading frames identified 94 ESTs potentially encoding OMTs, which assembled into 23 contigs, and included 12 singletons (not shown).

Example 6

Quantitative Real-Time RT-PCR Analysis

Given the likelihood that sorgoleone biosynthesis occurs primarily or exclusively in root hairs, a secondary screen using quantitative real-time PCR was employed to identify OMT sequences expressed specifically or predominantly in this cell type. Quantitative real-time PCR reactions were performed in triplicate using the GenAmp® 5700 Sequence Detection System (Applied Biosystems, Foster City, Calif.) as previously described (Baerson et al. 2005. *J. Biol. Chem.* 280: 21867-21881). First strand cDNAs were synthesized from 2 µg of total RNA in a 100 µL reaction volume using the TaqMan Reverse Transcription Reagents Kit (Applied Biosystems) per manufacturer's instructions. Independent PCR reactions were performed using the same cDNA for both the gene of interest and 18S rRNA, using the SYBR® Green PCR Master Mix (Applied Biosystems) with the following gene-specific primer pairs: SbOMT1-forward: 5'-GCATCTTCGT-TCATGTACTTGTTACAC-3' (SEQ ID NO:3), reverse: 5'-CGACGAAGCACATCCTTACTATGAG-3'(SEQ ID NO:4); SbOMT2-forward: 5'-GCG CCTCGTTTTCG-TATGC-3'(SEQ ID NO:5), reverse: 5'-GAA CATACAGCT-CACCTTCTC TGC-3'(SEQ ID NO:6); SbOMT3-forward: 5'-CAATTTCCCTTTTATGTTTAGCCTGA TAG-3'(SEQ ID NO:7), reverse: 5'-TGCCAGGGTGTGATATGTGC-3' (SEQ ID NO:8); polyubiquitin-forward: 5'-CTTCCTCT-GTCCCTCTGATGGAG-3' (SEQ ID NO:9), reverse: 5'-AA-GACACGACCACGACATGC-3'(SEQ ID NO:10); chlorophyll a/b-binding protein—forward: 5'-TGGATTGATTGATGCTGCAAG-3'(SEQ ID NO:11), reverse: 5'-CGTGAAACAAGAGACACACATGC-3'(SEQ ID NO:12); 18S rRNA-forward: 5'-GGCTCGAAGACGAT-CAGATACC-3'(SEQ ID NO:13), reverse: 5'-TCG-GCATCGTTTAT GGTT3'(SEQ ID NO:14). Primers were designed using Primer Express® software (Applied Biosystems) and the Amplify program (Engels, W. R. 1993. *Trends Biochem. Sci.* 18: 448-450). A dissociation curve was generated at the end of each PCR cycle to verify that a single product was amplified using software provided with the GeneAmp® 5700 sequence detection system. A negative control reaction in the absence of template (no template control) was also routinely performed in triplicate for each primer pair. The change in fluorescence of SYBR® Green I dye in every cycle was monitored by the GenAmp® 5700 system software, and the threshold cycle (CT) above background for each reaction was calculated. The CT value of 18S rRNA was subtracted from that of the gene of interest to obtain a $\Delta$ CT value. The CT value of an arbitrary calibrator (e.g., the tissue sample from which the largest $\Delta$ CT values were obtained) was subtracted from the $\Delta$ CT value to obtain a $\Delta\Delta$ CT value. The fold-changes in expression level relative to the calibrator were expressed as $2^{-\Delta\Delta CT}$.

Figure 3:
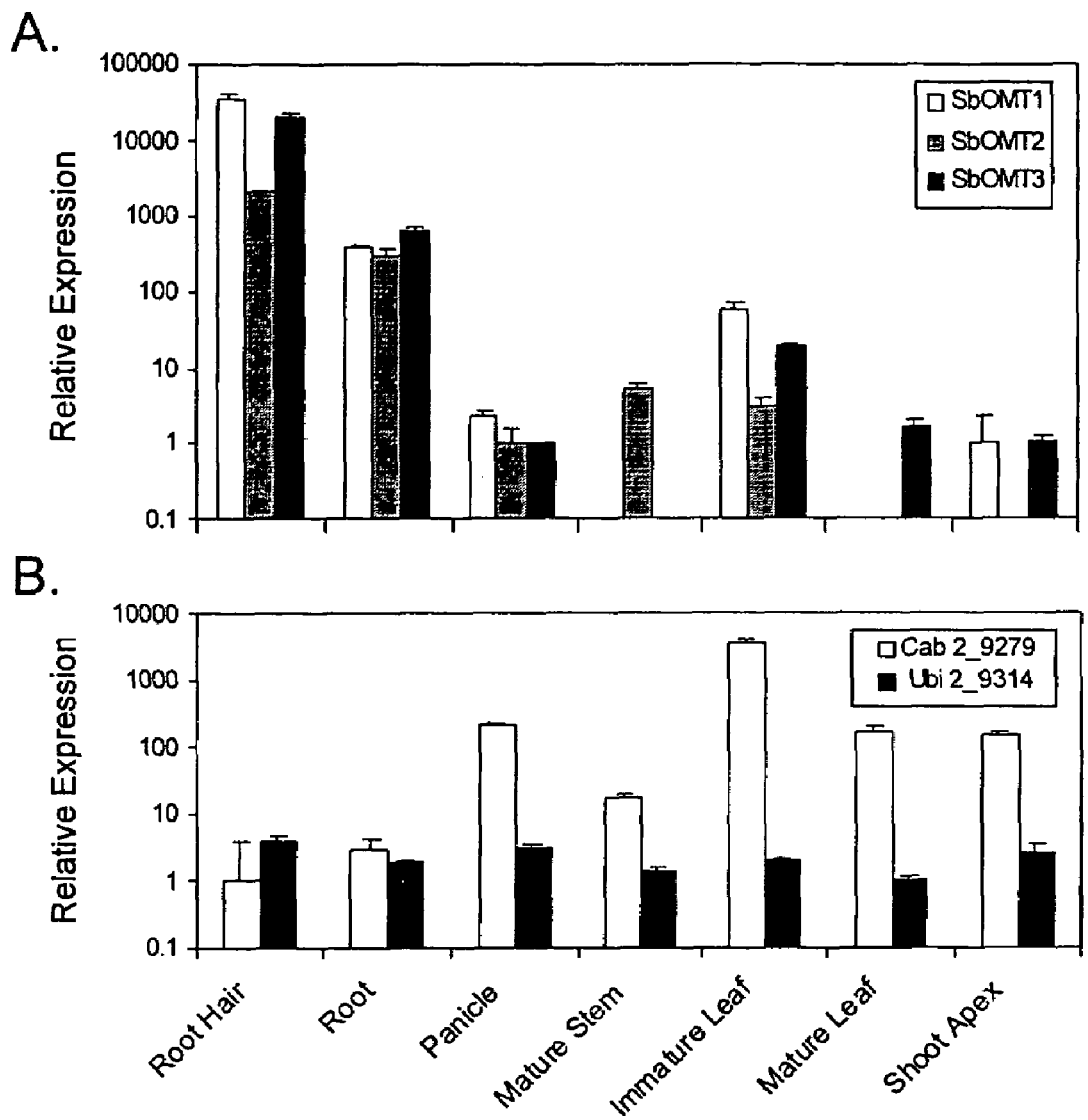
FIGS. 3A and 3B show the identification of root-hair-specific OMT sequences by quantitative real time RT-PCR analysis.

Gene-specific primer pairs were designed for monitoring OMT expression patterns in SYBR Green I-based real-time PCR assays, using cDNAs prepared from total RNAs isolated from root hairs, root systems, developing panicles, stems, immature and fully-expanded leaves, and shoot apices (FIG. 3). As controls, gene-specific primer pairs were also designed for a *S. bicolor* chlorophyll a/b-binding protein (cab) and polyubiquitin-like sequence, selected by in silico expression analysis using the MAGIC Gene Discovery Software (uniscript ID 2_9279 for cab, 2_9314 for polyubiquitin; Pratt et al., 2004). Based on these analyses, three of the OMT-like sequences we had identified in the data set were found to be predominantly expressed in root hair cells, as can be seen in FIG. 3 (designated SbOMT1, SbOMT2, and SbOMT3). For all three OMTs, steady-state RNA levels in root hairs were dramatically higher than all of the other tissues analyzed, with the exception of root systems, which were harvested from 8-day-old seedlings grown under identical conditions to those used for root hair preparations and contained extensive amounts of root hairs. In all cases, however, expression in root hairs was higher than that observed in roots, suggesting that the root hairs contributed a significant percentage of the transcripts detected in the total root samples. Specifically, SbOMT1 transcript levels were approximately 88-fold higher, SbOMT2 transcript levels were approximately 7-fold higher, and SbOMT3 transcript levels were approximately 32 fold higher in root hairs as compared with that observed for total root systems (FIG. 3). As expected, expression of the cab control sequence was detected predominantly in chloroplast-containing tissues, particularly in immature leaves, using the identical cDNA preparations prepared for the OMT expression studies described above (FIG. 3). For the polyubiquitin control, transcript levels were remarkably consistent among all of the samples analyzed, varying less than 4-fold between the highest and lowest samples (FIG. 3).

Example 7

Southern Blot Analysis

Genomic DNA from *S. bicolor* genotype Btx623 was prepared young leaf tissue using the Plant DNAzol Reagent (Invitrogen Corp., Carlsbad, Calif.). Approximately 1 g of powdered tissue was mixed with 3.0 mL Plant DNAzol reagent supplemented with RNase A at a final concentration of 1.0 mg mL$^{-1}$, then incubated at room temperature for 10 minutes with gentle shaking. The remainder of the extraction procedure was carried out per manufacturer's instructions, with an additional chloroform: isoamyl alcohol (24:1, v/v) extraction step performed prior to ethanol precipitation. Restriction endonuclease digestions and Southern blotting procedures were performed according to standard protocols (Sambrook et al., supra). Probe sequences approximately 450 by in length, corresponding to 3' UTR as well as some 3' coding sequence, were generated by PCR amplification from cloned SbOMT1, SbOMT2, and SbOMT3 cDNA templates with an Expand High Fidelity PCR kit (Roche Diagnostics Corporation) using a thermal profile of 94° C. for 30 s, then 55° C. for 1 min 30 s, followed by 72° C. for 1 min for 25 cycles. The following PCR primer pairs were used to generate probe sequences for the three *S. bicolor* OMTs: SbOMT1 forward: 5'-CACCAGAAGAAACACTAGCATCG-3'(SEQ ID NO:15), reverse: 5'-TTAAGGACCAATAAG-CAAGCTAGTACA-3'(SEQ ID NO:16); SbOMT2-forward: 5'-GAAGCACAGCTGCTGATGG-3'(SEQ ID NO:17), reverse: 5'-CAGCAAGCAACACACATCAAGTATG-3' (SEQ ID NO:18); and SbOMT3-forward: 5'-ATGACTG-GAGCAATGATGAGTG-3'(SEQ ID NO:19), reverse: 5'-CAGGGTGCCAGGG TGTG-3'(SEQ ID NO:20). The resulting PCR products were cloned using a Zero Blunt TOPO PCR Cloning Kit (Invitrogen Corp.) and confirmed by DNA sequence analysis. Prior to use in labeling reactions, probe sequences were excised from the cloning vectors by restriction endonuclease digestion and then gel-purified.

Figure 4A:
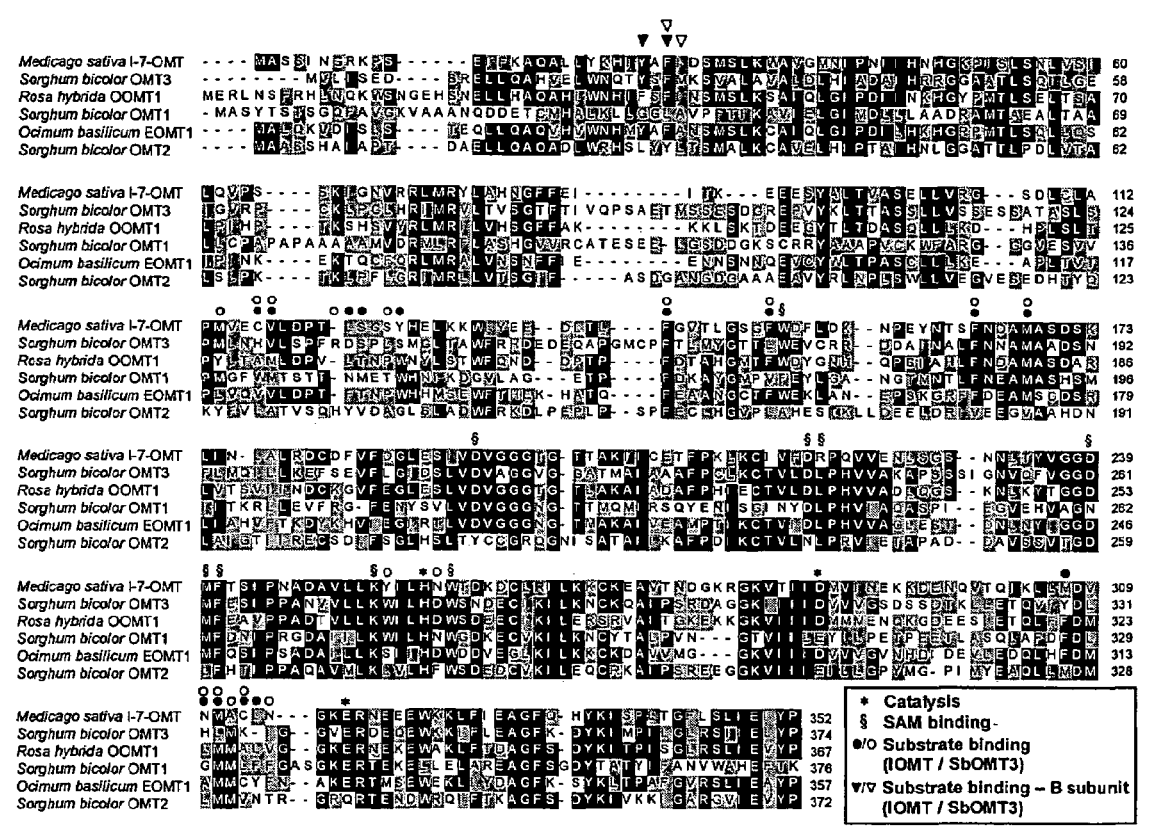
Figure 4B:
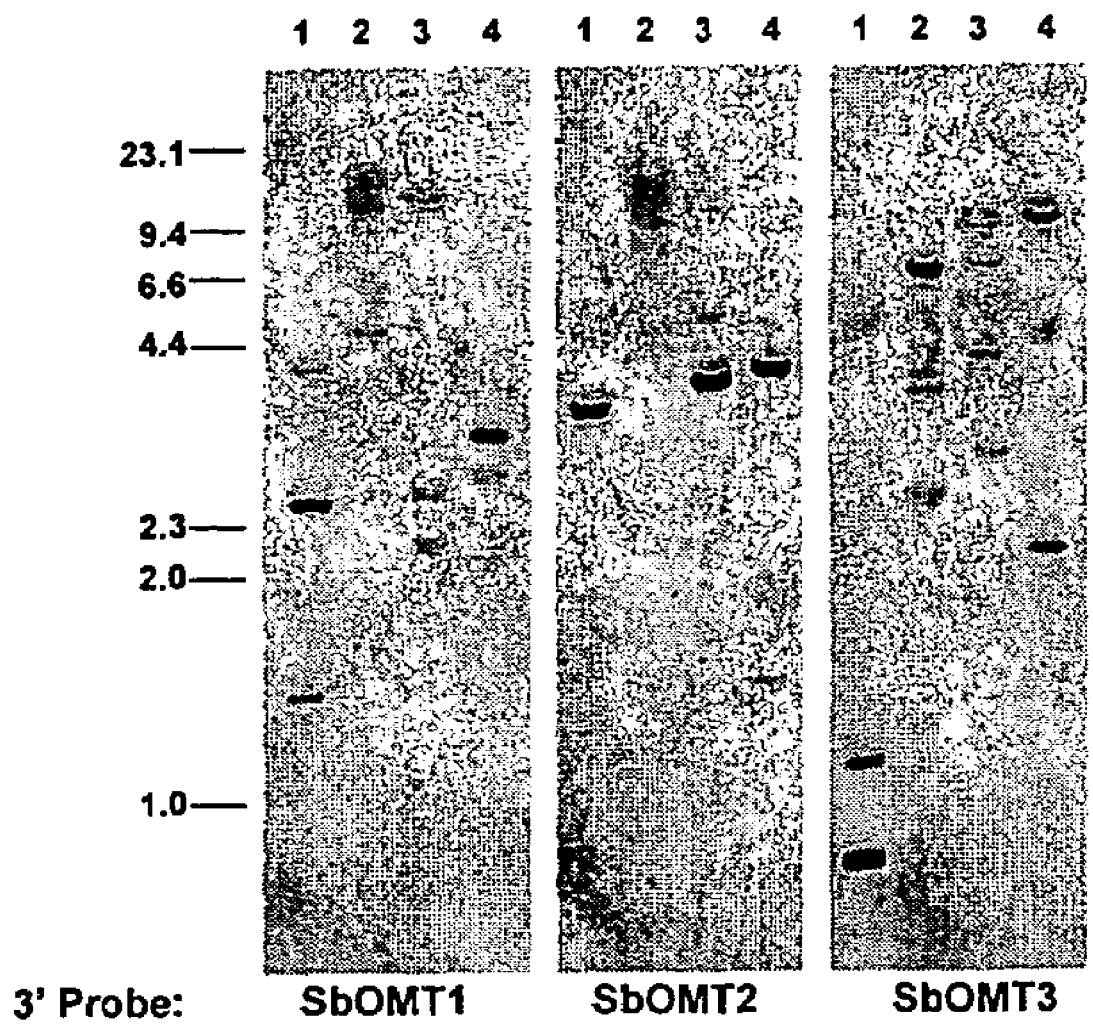
FIG. 4B shows the autoradiograph resulting 10 μgs of genomic DNA isolated from *S. bicolor* genotype BTX623 were digested with either DraI (lane 1), EcoRV (lane 2), ScaI (lane 3) or SphI (lane 4), then size-fractionated on 0.8% (w/v) agarose gels and transferred to nylon membranes. Blots were then hybridized using $^{32}$P-labeled 3' probe sequences for SbOMT1, SbOMT2 and SbOMT3, washed at high stringency, then subjected to autoradiography.

The deduced full-length open reading frames for SbOMT1, SbOMT2, and SbOMT3 exhibited extensive sequence similarity at the amino acid level to previously characterized plant type I S-adenosyl-L-methionine-dependent O-methyltransferases (Noel et al, supra) and contained the five conserved signatory motifs for this class of enzyme, as shown in the alignment in FIG. 4A. Southern analyses performed using approximately 450 by probe sequences derived from contiguous 3' UTR and coding regions for all three genes indicated that SbOMT1 and SbOMT2 likely do not share extensive nucleotide identity with other OMT genes within the *S. bicolor* genotype BTx623 genome (FIG. 4B). For SbOMT3, the hybridization patterns obtained suggest the existence of one or more closely related OMT sequences in BTx623, based on the high-stringency wash conditions employed.

Example 8

Heterologous Expression and Purification of Recombinant OMTs

DNA manipulations and *E. coli* transformation protocols used during the preparation of plasmid vectors for recombinant OMT experiments were performed according to standard procedures (Sambrook et al., supra). Coding sequences for SbOMT1 and SbOMT3 were obtained from full-length cDNA clones identified from the root hair cDNA library described above. The open reading frame for SbOMT2 was determined from an assembly of sequence data obtained from 5'-truncated clones within the root hair cDNA library with EST data obtained from the *Sorghum* Milestone Unigene data set (Pratt et al., supra). *E. coli* overexpression vectors were constructed by PCR amplification of SbOMT1, SbOMT2, and SbOMT3 coding regions using PCR primers designed with flanking NdeI (forward primer) and BamHI (reverse primer) restriction sites to facilitate direct cloning into pET15b (EMD Biosciences, La Jolla, Calif.), using the following PCR primer pairs: SbOMT1-forward: 5'-GCAATTC-CATATGGCCA GCTATACTAGTACTAGTGG-3'(SEQ ID NO:21), reverse: 5'-GACTAGGGATCCTCACT TTGT-GAATTCATGGG-3'(SEQ ID NO:22); SbOMT2-forward: 5'-GCAATTCCATATGG CCGCGTCTTCTCATGC-3'(SEQ ID NO:23), reverse: 5'-GACTAGGGATCCTTATGGGT AGACTTCGATGACACCAC-3'(SEQ ID NO:24); and SbOMT3-forward: 5'-GCAATTCC ATATGGTACTCAT-CAGCGAGGAC-3'(SEQ ID NO:25), reverse: 5'-GAC-TAGGGATCC TCATGGATATAGCTCAATGATCG-3' (SEQ ID NO:26). Primers were added at a final concentration of 0.4 mM to 50 µL PCR reactions, using 2 µL of first-strand cDNA as template, prepared from root hair total RNA with a SuperScript First-Strand Synthesis System (Invitrogen Corp.) per manufacturer's instructions. PCR amplifications were performed with an Expand High Fidelity PCR kit (Roche Diagnostics Corp.), using a thermal profile of 94° C. for 30 seconds, then 55° C. for 2 minutes, followed by 75° C. for 3 minutes, for a total of 30 cycles. The resulting PCR products were then gel-purified, digested with NdeI and BamHI, then ligated with NdeI and BamHI-digested pET15b, resulting in the final overexpression vectors containing the three *S. bicolor* OMT predicted open reading frames, as confirmed by DNA sequence analysis. The expression vectors were then transformed into strain *E. coli* strain BL21/DE3 (EMD Biosciences, La Jolla, Calif.) for recombinant enzyme studies.

For recombinant protein production, *E. coli* cultures were grown at 37° C. to an optical density of 0.6 at 600 nm, then induced with 0.5 mM IPTG and allowed to grow 5 additional hours at 25° C. Cells were harvested by centrifugation at 3000×g for 20 min at 4° C., washed with cold 0.9% NaCl, then collected by re-centrifugation at 3000×g. Pellets were resuspended in cold lysis buffer (50 mM Tris-HCl, pH 7.5, 1 M NaCl, 5 mM imidazole, 10% glycerol, 1 µg/ml leupeptin), and extracted using a French press (Thermo IEC, Needham Heights, Mass.) at a pressure of 10,000 kPa. Benzonase (25 U/ml) and 1 mM PMSF were added immediately to the lysate. After 15 min incubation at room temperature, lysates were centrifuged at 15,000×g for 20 min, and the supernatant was loaded onto His GraviTrap columns (Amersham Biosciences, Piscataway, N.J.) activated with 2 mL of 0.1 M NiSO4 and washed with 10 mL of distilled water. The Ni-column was previously equilibrated with 10 mL buffer A (20 mM Tris-HCl, pH 8.0, 500 mM NaCl, 5 mM imidazole). The column was washed with 4 mL buffer A following each 2 mL of supernatant added. Once sample loadings were complete, the columns were washed with 8 mL of buffer A, followed by 8 mL of buffer B (20 mM Tris-HCl, pH 8.0, 500 mM NaCl, 100 mM imidazole) to remove non-specifically bound proteins. Recombinant proteins were then eluted with 2.5 mL of elution buffer (20 mM Tris-HCl, pH 8.0, 500 mM NaCl, 250 mM imidazole). Columns were washed with 10 mL wash buffer C (20 mM Tris-HCl, pH 8.0, 500 mM NaCl, 1 M imidazole), followed by 10 mL of distilled water after each use to remove contaminating proteins. Recombinant protein-containing fractions (250 mM imidazole) were desalted on a PD-10 column equilibrated with cold desalting buffer (20 mM Tris-HCl, pH 7.5, 10 mM DTT, 10% glycerol). Protein concentrations were determined using a Bio-Rad protein assay kit (Bio-Rad Laboratories, Hercules, Calif.). Enzyme preparations were stored at ±80° C. prior to use.

Example 9

OMT Enzymatic Assays

Substrate specificities and kinetic parameters for recombinant OMTs were determined using to a modified protocol based on Wang and Pichersky (1999. *Arch. Biochem. Biophys.* 368: 172-180). All enzymatic assays consisted of 90 µL of assay buffer (250 mM Tris-HCl, pH 7.5, 10 mM DTT), 200 µL of purified enzyme preparation (200 µg protein/ml in), 5 µL of a 10 mM substrate stock solution (dissolved in 100% ethanol), and 5 µL of S-[methyl-$^{14}$C] adenosyl-L-methionine (40-60 mCi/mmol, 0.1 mCi/ml; ICN Biomedicals, Irvine, Calif.). Reactions were incubated for 30 min at 30° C. using a Thermomixer (Brinkman Instrument, Westbury, N.Y.), then quenched by addition of 25 µL of 6 N HCl. Radiolabeled products were subsequently extracted by the addition of 1 mL of hexane:ethyl acetate (1:1 vol/vol), and 300 µL of the (upper) organic phase were transferred to scintillation vials containing 5 mL of Ultima Gold scintillation fluid (Packard Bio-Science, Meriden, $C_T$). Scintillation counts were performed using a Tri-Carb 1600TR Liquid Scintillation Analyzer (Packard BioScience). Protein concentrations and time points used for activity measurements were controlled to insure linearity of the assays. Kinetic parameters were determined from assays performed in triplicate as described above, but with substrate concentrations ranging from 10 µM to 10 mM. Data from enzyme kinetics experiments were fit to the Michaelis-Menten equation using the SigmaPlot v. 9.01 enzyme kinetics module (Systat Software, Inc., Point Richmond, Calif.).

Based on the real-time PCR results described above, SbOMT1, SbOMT2, and SbOMT3 were chosen for follow-up recombinant enzyme studies to determine their preferred substrates.

To determine the effect of SbOMT3 on pterostilbene biosynthesis, the three cloned O-methyltransferase genes were expressed and the recombinant enzymes were reacted with resveratrol (FIG. 7A). The products from these reactions were then chemically analyzed by gas chromatography/mass spectroscopy. The enzyme SbOMT1 reacted with resveratrol; however, resveratrol was not methylated in the correct position to produce pterostilbene. Thus, only about 2% of the product obtained was pterostilbene; 88% was 3,5-dihydroxy-4'-methoxystilbene (FIG. 7B). SbOMT2 did not react with resveratrol at all. SbOMT3 is an efficient generator of pterostilbene; 96% of the product obtained from the reaction of SbOMT3 and resveratrol is pterostilbene (FIG. 7C). Further, enzyme kinetic data indicate that both SbOMT1 and SbOMT3 use resveratrol as a substrate (Table 1. FIG. 8). However, only SbOMT3 methylates resveratrol in the correct position to produce pterostilbene to any significant extent.

TABLE 1

Enzymatic Activity for Recombinant SbOMT1 and SbOMT3 with Resveratrol.

| Gene | Km (µM) | V max (nmol mg$^{-1}$ h$^{-1}$) | Kcat (s$^{-1}$) | Kcat/Km (M$^{-1}$s$^{-1}$) |
|---|---|---|---|---|
| SbOMT3 | 70.9 ± 9.2 | 8.3 ± 0.7 | 1.0 × 10$^{-4}$ | 1.4 |
| SbOMT1 | 16.9 ± 1.2 | 8.4 ± 0.1 | 1.0 × 10$^{-4}$ | 5.9 |

A panel of benzene-derivatives containing different functional groups and substitution patterns were tested in enzyme assays with all three recombinant enzymes (Table 2), including a series of 5-n-alkylresorcinols of increasing chain length, as well as 5-n-pentadecatrienyl resorcinol, the proposed sorgoleone pathway intermediate and in vivo substrate for the participating OMT enzyme (FIG. 1). For these analyses, full-length open reading frames for all three OMTs were overexpressed in *E. coli* as N-terminal polyhistidine fusions, purified using an activated Ni-column, then radiometrically assayed in the presence of different substrates as described by Wang and Pichersky (1999, supra), with slight modifications. The results of these experiments are shown in Table 2.

TABLE 2

Relative Activity (%) of Recombinant SbOMT1 and SbOMT3 with Various Substrates

| Substrate | SbOMT1 | SbOMT3 |
|---|---|---|
| Resorcinol monomethyl ether [R: H] | 24.8 ± 1.1 | 3.2 ± 0.7 |
| Orcinol monomethyl ether [R: CH$_3$] | 49.6 ± 1.6 | 3.5 ± 0.5 |
| Guaiacol [R: H] | 7.8 ± 0.5 | 3.2 ± 0.6 |
| Eugenol [R: CH$_2$CH=CH$_2$] | 100 ± 5.2$^a$ | 3.2 ± 0.5 |
| Ferulic acid [R: CH=CHCOOH] | 3.1 ± 0.3 | 3.5 ± 0.6 |

TABLE 2-continued

Relative Activity (%) of Recombinant SbOMT1 and SbOMT3 with Various Substrates

| | Substrate | SbOMT1 | SbOMT3 |
|---|---|---|---|
| 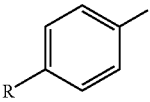 | 4-Methoxyphenol [R: $OCH_3$]<br>p-Coumaric acid [R: $CH=CHCOOH$] | 8.3 ± 0.5<br>0 | 3.3 ± 0.6<br>3.5 ± 0.4 |
| 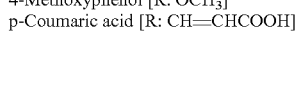 | Catechol [R: H]<br>Caffeic acid [R: $CH=CHCOOH$] | <1.0<br><1.0 | 3.6 ± 0.6<br>3.6 ± 0.6 |
| 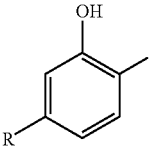 | n-Alkylresorcinolic series<br>Resorcinol [R: H]<br>Orcinol [R: $CH_3$]<br>5-n-Propyl-resorcinol [R: $(CH_2)_2$—$CH_3$]<br>5-n-Butyl-resorcinol [R: $(CH_2)_3$—$CH_3$]<br>5-n-Pentyl-resorcinol [R: $(CH_2)_4$—$CH_3$]<br>5-n-Hexyl-resorcinol [R: $(CH_2)_5$—$CH_3$]<br>5-n-Heptyl-resorcinol [R: $(CH_2)_6$—$CH_3$]<br>5-n-Nonyl-resorcinol [R: $(CH_2)_8$—$CH_3$]<br>5-n-Pentadecyl-resorcinol [R: $(CH_2)_{14}$—$CH_3$]<br>5-n-[8', 11', 14']-Pentadecatrienyl-resorcinol<br>[R: $(CH_2)_7$—$(CH=CH-CH_2)_2$—$CH=CH_2$] | <1.0<br>1.3 ± 0.7<br>2.2 ± 0.9<br>1.1 ± 0.1<br><1.0<br>0<br>0<br>0<br><1.0<br>— | 4.1 ± 0.1<br>4.5 ± 0.1<br>11.8 ± 0.2<br>42.0 ± 1.2<br>100 ± 2.2$^a$<br>79.4 ± 7.6<br>27.2 ± 1.3<br>3.3 ± 0.8<br>5.0 ± 0.4<br>14.9 ± 4.3 |

$^a$100% activity for SbOMT1 and SbOMT3 corresponds to 1.1 and 11.1 pmol $sec^{-1}$ $mg^{-1}$ protein, respectively.

For SbOMT1, eugenol was clearly the preferred substrate, but significant activity was also obtained with the monomethyl ethers of orcinol and resorcinol. Aside from all three compounds containing a methoxy group and a simple benzene ring, it is difficult to discern a clear pattern governing the substrate specificity for SbOMT1. For example, guaiacol, ferulic acid, and 4-methoxyphenol all possess a single benzene ring containing a methoxy group, yet were much less efficiently utilized by recombinant SbOMT1. By definition, SbOMT1 could be classified as a eugenol OMT (EOMT), functionally related to the previously characterized EOMT isolated from sweet basil (Gang et al., supra), and the (iso) EOMT isolated from *Clarkia breweri* (Wang et al. 1997. *Plant Physiol.* 114: 213-221). The substrate specificity of SbOMT1 is particularly reminiscent of that observed for EOMT from sweet basil, which also efficiently utilized guaiacol, but exhibited little to no detectable activity with resorcinol, caffeic acid, ferulic acid, or catechol. The sweet basil enzyme did efficiently use chavicol as a substrate, which lacks the methoxy ring substituent, however chavicol is otherwise structurally identical to eugenol (Gang et al., supra). Recombinant SbOMT2, in contrast to SbOMT1 and SbOMT3, showed no detectable activity against any of the substrates indicated in Table 2.

In contrast to SbOMT1, the substrate specificity for SbOMT3 indicated a clear preference for the alkylresorcinolic substrates listed in Table 2. SbOMT3 enzyme activity increased dramatically as the substrate alkyl side chain was increased up to five carbons in length, and near-maximal activity was observed using hexyl resorcinol, after which enzyme activity decreased precipitously with increasing side chain length (Table 2). Evaluation of steady-state kinetic parameters for reaction of SbOMT3 with C3-C7 alkylresorcinols (Table 3) suggested an increase in both the enzyme's affinity for these substrates (Km) with increasing chain length, as well as an increase in catalytic efficiency (kcat/Km). Interestingly, activity of SbOMT3 with the proposed sorgoleone pathway intermediate, 5-pentadecatrienyl resorcinol (FIGS. 1, 2), was approximately 3-fold higher than that for the 5-pentadecyl resorcinol, which contains a saturated (alkyl) side chain of identical length (Table 2).

TABLE 3

Kinetic Parameters for Recombinant SbOMT3 with Alkylresorcinols and Co-substrate (SAM).

| Substrate | Alkyl Group | $K_m$ (μM) | V max (nmol $mg^{-1}$ $h^{-1}$) | Kcat ($s^{-1}$ × $10^4$) | Kcat/Km ($M^{-1}s^{-1}$) |
|---|---|---|---|---|---|
| 5-n-Propyl-resorcinol | $C_3$ | 1436 | 15.6 | 1.9 | 0.13 |
| 5-n-Butyl-resorcinol | $C_4$ | 481 | 33.0 | 3.9 | 0.81 |
| 5-n-Pentyl-resorcinol | $C_5$ | 152 | 39.2 | 4.7 | 3.1 |
| 5-n-Hexyl-resorcinol | $C_6$ | 72 | 25.2 | 3.0 | 4.2 |
| 5-n-Heptyl-resorcinol | $C_7$ | 23 | 10.4 | 1.2 | 5.2 |
| SAM | | 67.5 | | | |

The alk(en)ylresorcinols used for the present study have not been previously tested as substrates in other OMT studies performed to date. While it is not possible to draw direct parallels between SbOMT3 and other characterized OMT enzymes, it is likely however, that SbOMT3 represents a novel subclass of type I plant-specific OMT enzymes, exhibiting a substrate profile that has not previously been demonstrated for any plant OMT to our knowledge.

Example 10

Homology Modeling and Automated Substrate Docking

Figure 6:
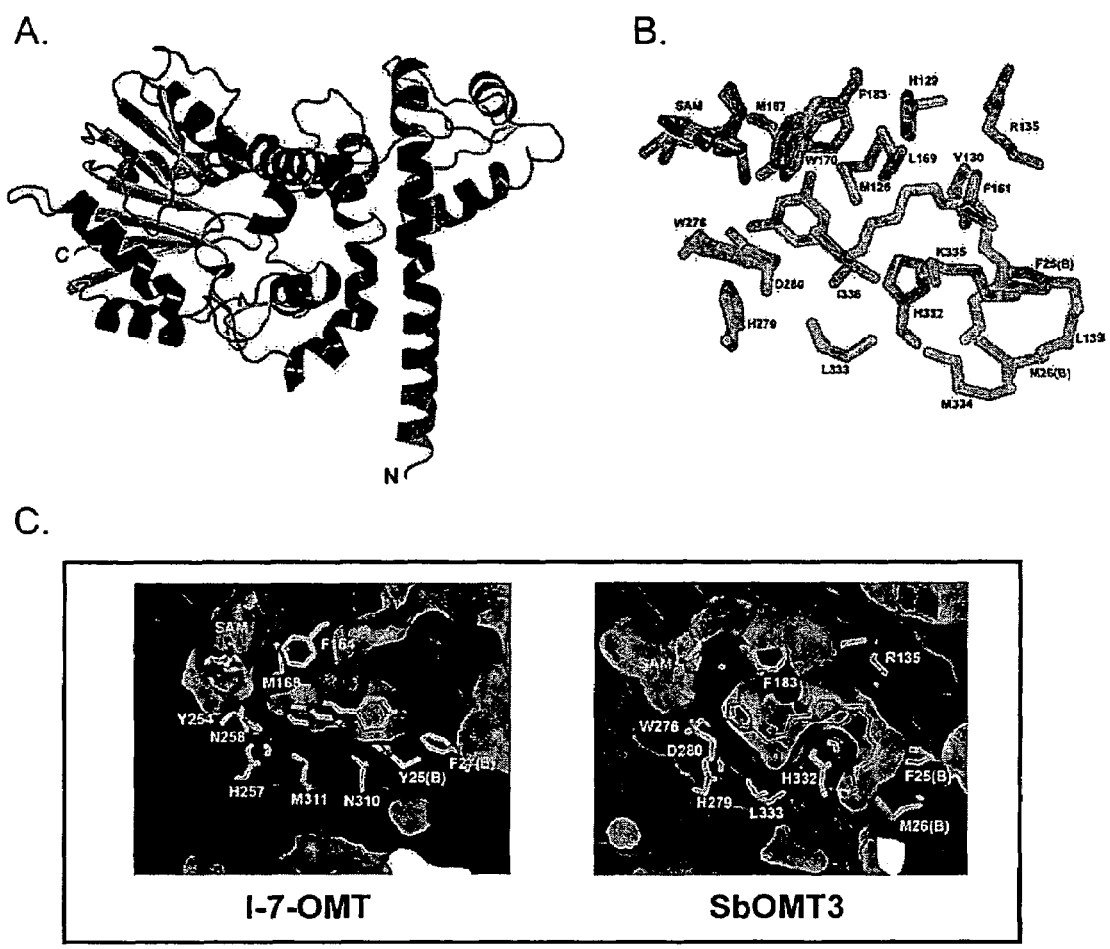
FIGS. 6A-6C depict molecular modeling of SbOMT3 based on the *M. sativa* I-7-OMT crystal structure.

To examine the potential structural basis for the observed substrate specificity of SbOMT3, computational homology modeling and automated substrate dockings were also performed (FIG. 6). Several plant type I OMT crystal structures have been previously determined (Zubieta et al. 2001, 2002, supra; Liu et al., in preparation), which provide a useful basis for an in silico homology-based structure-function analysis of OMT homologues. Among the crystallized proteins, the alfalfa (*Medicago sativa*) isoflavonoid 7-O-methyltransferase (I-7-OMT) revealed the highest relationship score with SbOMT3 (37% identity), and therefore its crystal structure (PDB code: IFP2) was used to model SbOMT3.

The SbOMT3 amino acid sequence was aligned to *M. sativa* I-7-OMT using Clustal W (version 1.82). The model of SbOMT3 was built as described (Coiner et al. 2006. *Plant J.* 46: 193-205), using the MODELER software package (Marti-Renom et al. 2000. *Annu. Rev. Biophys. Biomol. Struct.* 29: 291-325; Fiser et al. 2000. *Prot. Sci.* 9: 1753-1773), with SAH and formononetin complexed to I-7-OMT (PDB code 1FP2) as the structural template. For docking analysis, the Genetic Optimization for Ligand Docking (GOLD) program (CCDC Software Ltd, Cambridge UK) was employed. The parameters controlling the precise operation of the genetic algorithm were set as described previously (Coiner et al., supra). The validity of the settings was first confirmed as follows: the isoformononetin bound in the active site of the I-7-OMT model was removed, and the isoflavone daidzein was then docked to the structure to compare the in silico docking solutions to the actual structural complex. The confirmed settings were then used for the automated docking of 5-(8',11',14')-pentadecatrienyl resorcinol to the SbOMT3 model. The size of the SbOMT3 active site was defined within 15 Å around the NE2 atom of H322 which projects into the center of the putative substrate binding site of the SbOMT3 model. Ten docking calculations were run and the GOLD score was used to identify the lowest energy docking results.

Similar to the *M. sativa* I-7-OMT (Zubieta et al. 2001, supra), the overall structure of the SbOMT3 model (FIG. 6A) indicates a small N-terminal domain that, as in the other type I OMTs, likely plays a major role facilitating the dimerization of the two subunits within the homodimer. The larger C-terminal domain contains both the SAM and the substrate binding sites. The SbOMT3 substrate docking model with 5-(8, 11,14)-pentadecatrienyl resorcinol (FIG. 6B) shows the best fit with the 3-hydroxyl group of the resorcinol head pointing to the methyl donor SAM and H279, consistent with the histidine functioning as general base in the deprotonation of the hydroxyl nucleophile in type I OMTs (Zubieta et al. 2001, 2002, Liu et al., supra). The binding of the resorcinolic substrates appears to be primarily by van der Waals hydrophobic interactions, with the resorcinol ring positioned by a series of hydrophobic residues (M126, F183, M187, 1336, and the side chains of W170 and W276; FIG. 6B). V130 and F161 form a hydrophobic sandwich-like clamp that constrains the center portion of the aliphatic side chain, while the tip of the very hydrophobic alkyl portion protrudes into a hydrophobic cave formed at the protein dimer interface by the side chains of K335, M334, L139 (from protein subunit A), and F25 and M26 (from subunit B).

The positioning and binding of the methyl donor SAM and the location of the putative catalytic histidine (H279; FIG. 6B) is very similar to that in the crystallized proteins, indicating that SbOMT3 uses the same SN2 catalytic mechanism for methyl transfer as proposed for the other enzymes. However, the active site architecture of SbOMT3 (FIG. 6B) reveals significant differences with that of the *M. sativa* 1-7-OMT, most readily visible by comparison of the active site surface views of the two enzymes (FIG. 6C). Most notable is the position of the side chain of H332 in SbOMT3 (corresponding to N310 in I-7-OMT) which projects into the binding site's center, producing a curved cavity appearing particularly well suited to accommodate the stereochemical conformation of the physiological substrate 5-pentadecatrienyl resorcinol (FIG. 1). The observation that the otherwise very similar substrate 5-pentadecyl resorcinol possessing a saturated alkyl side chain is a poorer substrate (Table 2), suggests that the shape of the cavity plays a significant role in determining the substrate preferences. Furthermore, given the size of the active site cavity, it is not surprising that non-physiological substrates possessing a resorcinol head but shorter alkyl side chains are also excellent substrates of SbOMT3 (Table 2).

Example 11

Substrates 5-n-Pentadecyl resorcinol was purchased from Chem Service, Inc. (West Chester, Pa.). For preparation of all other 5-n-alkylresorcinols described in this work, 3,5-bis-(benzyloxy)benzaldehyde was first prepared from methyl 3,5-dihydroxybenzoate (Lancaster Synthesis, Inc., Pelham, N.H.) using the method developed by Franke and Binder (1980. *Helvetica Chimica Acta* 63: 2508-2514). A mixture of the appropriate alkyltriphenylphosphonium bromide (5 mmol) (Lancaster Synthesis, Inc.) with NaH (5 mmol) was stirred for 15 min at room temperature in dry methylene chloride, then 3,5-bis(bezyloxy)benzaldehyde (5 mmol) was added. The reaction mixture was refluxed for 4 h, filtered, and evaporated. The residue obtained was chromatographed over silica gel, and eluted with hexane:ethyl acetate (49:1 vol/vol), to afford a mixture of cis and trans 1-(2-alkenylinyl)-3,5-dihydroxybenzene isomers in 70-80% yield. The mixtures were hydrogenated at 275 kPa for 10 h in the presence of 10% palladium-carbon catalyst, filtered through celite, and then evaporated. Residues were then chromatographed over silica gel and eluted with hexane:ethyl acetate (17:3 vol/vol), quantitatively yielding the final n-alkylresorcinol product. The identities of all compounds were confirmed using both physical and spectroscopic methods, including $^1$H-NMR, $^{13}$C-NMR, and high-resolution mass spectroscopy (HR-MS). $^1$H-NMR and $^{13}$C-NMR spectra were recorded using an Avance DPX-300 spectrometer (300 MHz for $^1$H NMR, 75.45 MHz for $^{13}$C NMR; Bruker Biospin Corp., Billerica, Mass.) and an Avance DRX-500 spectrometer (500 MHz for $^1$H NMR, 125 MHz for $^{13}$C NMR; Bruker Biospin Corp.) in CDCl$_3$ and MeOH-D4, using tetramethyl-silane as an internal standard. HR-MS data were obtained by direct probe, using a Bioapex-FTMS spectrometer with electrospray ionization (Bruker Biospin Corp.).

5-n-[8',11',14']-Pentadecatrienyl resorcinol was purified from *Anacardium occidentale* (cashew) nutshell liquid using the method developed by Paramashivappa et al. (2001). All other substrates described were purchased from Sigma-Aldrich Corp. (St. Louis, Mo.).

Example 12

Phylogenetic Analysis

Amino acid sequences of putative O-methyltransferases were retrieved from the NCBI non-redundant peptide sequence database (ncbi.nlm.nih.gov) by BLASTP analysis and from the TIGR plant gene indices database (tigr.org) by TBLASTN analysis, using default parameters. A candidate list was screened for redundancy and errors, resulting in a data set comprised of 134 sequences, including the three *S. bicolor* O-methyltransferases sequences described in this work (SbOMT1, SbOMT2, and SbOMT3). Multiple sequence alignments were constructed with ClustalX ver. 1.81 (Thompson et al. 1997. *Nucleic Acids Res.* 25: 4876-4882). Three parameter sets were investigated to assess sensitivity of the alignment to gap costs: default (gap opening=10.0, gap extension=0.2); gap opening=10.0, gap extension=1.0; gap opening=1.0, gap extension=1.0. All other parameters were set at default values (in particular, the Gonnet weight matrix was employed). The alignments differed dramatically in length (853, 698, and 817 residues, respectively).

Figure 5:
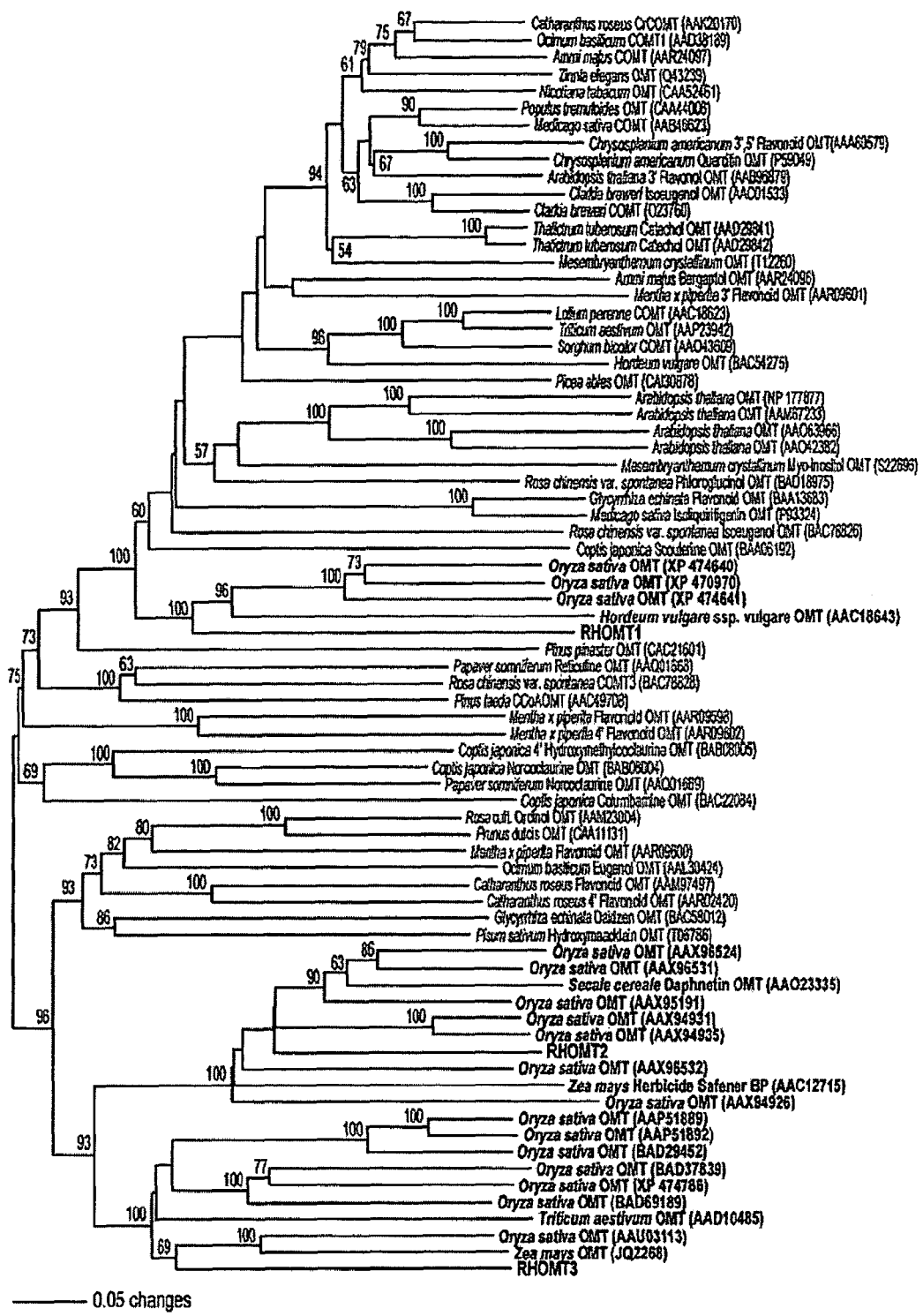
FIG. 5 shows a phylogenetic analysis of SbOMT1, SbOMT2, and SbOMT3 relatives. The phylogram was generated using the neighbor-joining method as implemented in PAUP ver 4.0b10 (Swofford, D. 2001. PAUP. Version 4. Sinauer Associates, Sunderland, Mass.). The bootstrap method was performed for 5000 pseudoreplicate data sets. Numbers shown at the tree forks indicate frequency of occurrence among all bootstrap iterations performed.

Phylogenetic estimates of the relationships among sequences were conducted separately for each alignment. The neighbor-joining method (Saitou and Nei. 1987. *Mol. Biol. Evol.* 4: 406-425) as implemented in PAUP* ver. 4.0b10 (Swofford, supra) was used to estimate trees. Default parameters were used except that ties were broken randomly. Trees were midpoint rooted and nodal support was estimated by the bootstrap (Felsenstein, J. 1985. *Evolution* 39: 783-791), employing 5000 pseudoreplicate data sets. Phylogenetic trees estimated from the three alignments (not shown) were extremely similar with differences restricted to minor rearrangements within clades and the relationships among several moderately sized clades. The third alignment, with equivalent gap opening and extension penalties, was selected for discussion and further analysis. However, all interpretations made here would be identical on trees estimated from the other two alignments. To clarify relationships in the presentation of the results, the 134 sequences in the third alignment were reduced to 75 sequences by removing highly similar sequences and reducing representation in clades distantly related to SbOMT1, SbOMT2, and SbOMT3. The resulting alignment was reanalyzed using the same methods and the estimated phylogeny (FIG. 5), and was highly congruent with the estimate from the 134-sequence data set.

Example 13

Plant Transformation

Pterostilbene Production in Transgenic Tobacco

A two-gene strategy was devised for the production of pterostilbene in transgenic plants. The first gene is capable of producing resveratrol in vivo from ubiquitously available precursors. The resultant resveratrol is then available to serve as substrate for SbOMT3, yielding pterostilbene. Stilbene synthase from the peanut plant (*Arachis hypogaea*) represents one enzyme capable of producing resveratrol from the common precursors coumaryl-CoA and malony-CoA (Schroder et al., supra).

Figure 9:
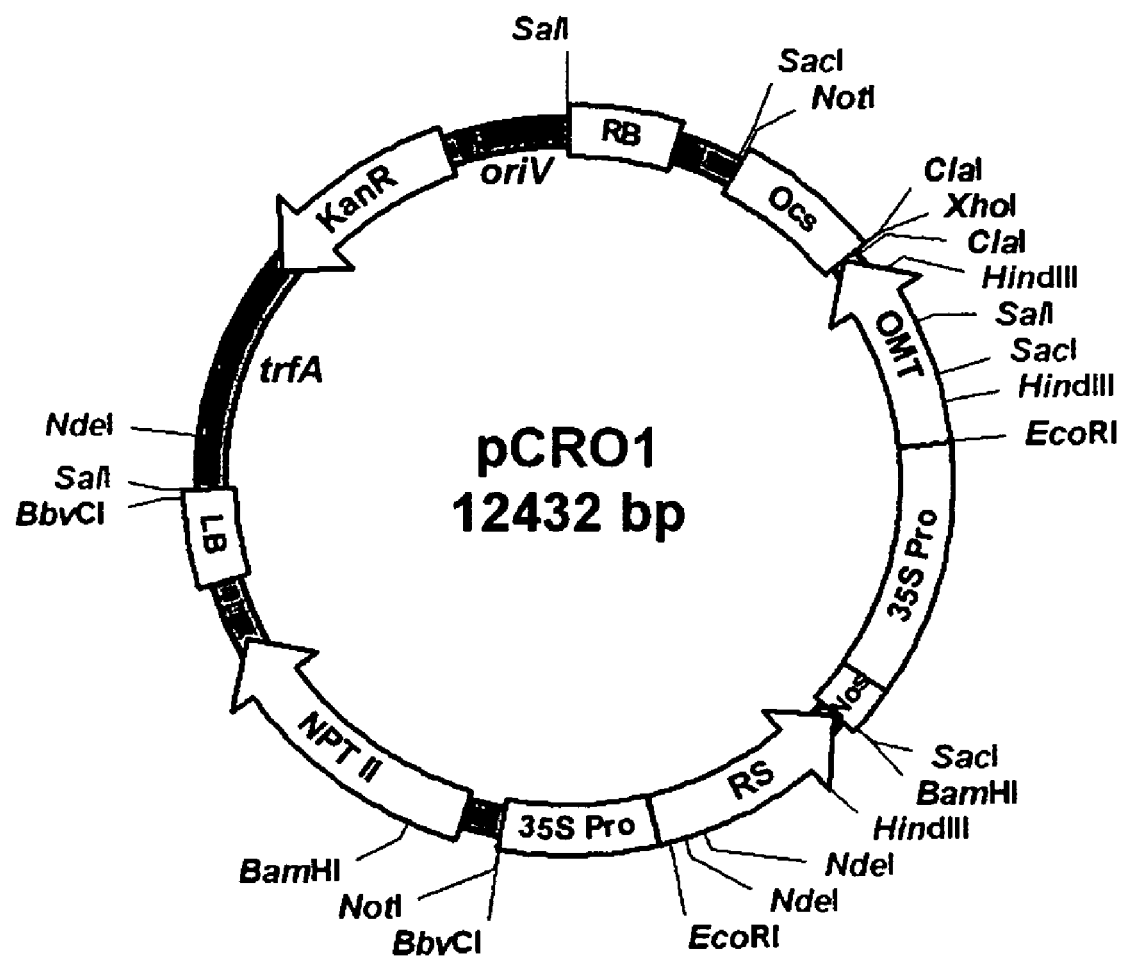
FIG. 9 depicts the two-gene binary pCRO1 vector for the production of pterostilbene in plants.

A binary, vector was developed to simultaneously express both the peanut stilbene synthase enzyme and SbOMT3 in planta (FIG. 9). For this approach, the complete open reading frame of peanut stilbene synthase (GenBank Accession No. AAA96434) was positioned downstream of the CaMV 35S promoter, and directly upstream of the polyadenylation region of the *A. tumefaciens* nopaline synthase gene. Similarly, the complete open reading frame for SbOMT3 was cloned downstream of the CaMV 35S promoter, and directly upstream of the polyadenylation region of the *A. tumefaciens* octapine synthase gene (FIG. 9). Both transgene cassettes were cloned within the T-DNA borders of a vector derived from pCB302 (Xiang et al. 1999. *Plant Mol. Biol.* 40:711-717). The resulting construct, shown in FIG. 9, contains the two expression cassettes arranged in a head-to-tail orientation and was designated pCRO1. All DNA manipulations involved in the construction of pCRO1 involved standard cloning procedures (Sambrook et al., supra).

To generate transgenic plants simultaneously expressing the peanut stilbene synthase and sorghum O-methyltransferase SbOMT3 enzymes, the plasmid pCRO1 (FIG. 9) was first transformed into the *Agrobacterium tumefaciens* strain EHA105 (Hood et al. 1993. *Trans. Res.* 2:208-218) using the freeze-thaw method devised by An et al. (1988. In: *Plant Molecular Biology Manual*, S. B. Gelvin and R. A. Schilperoort (eds.) Kluwer Academic Publishers, Dordrecht, Pages A3 1-13). As a control, an "empty vector" identical to pCRO1, but lacking the inserted stilbene synthase and SbOMT3 expression cassettes, was also transformed into *A. tumefaciens* strain EHA105.

Recombinant *A. tumefaciens* strains harboring pCRO1, or the parent ("empty") vector control were co-cultivated with leaf disk explants derived from *Nicotiana tabacum* (cv. Wisconsin 38), and transgenic tobacco plants were generated under kanamycin selection from independent calli using the method described by Horsch et al. (1988. In: *Plant Molecular Biology Manual*, S. Gelvin and R. Schilperoort (eds.), Kluwer Academic Publishers, Dordrecht, Pages A5 1-9). After the initial co-cultivation period, carbenicillin was also added to tissue culture plates at a final concentration of 200 µg/ml as a counter-selective agent against *agrobacterium*. Following the regeneration of root systems, putative transformants were transferred to soil and maintained in a greenhouse for seed collection. The resulting seed from the primary transformant lines were surface sterilized and germinated on MS plates containing 75 µg/ml kanamycin, to both confirm transformation and examine the inheritance of the kanamycin antibiotic resistance marker (Horsch et al., supra).

To confirm the expression of both the peanut stilbene synthase and O-methyltransferase SbOMT3 expression cassettes in the various transgenic tobacco lines generated, quantitative real-time PCR analyses were performed using leaf tissues samples as previously described (Baerson et al., supra). Total RNAs prepared for use in real-time PCR assays were isolated from flash-frozen, pulverized transgenic leaf samples using the Trizol reagent (Invitrogen Corp., Carlsbad, Calif.), with an additional homogenization step of 30 s at 25,000 rpm using a handheld homogenizer. The RNA recovered was then re-purified with a RNeasy Plant Mini-Kit (Qiagen Inc., Valencia, Calif.) per manufacturer's instructions. RNA recovery and purity were determined spectrophotometrically, and sample integrity was assessed by agarose gel electrophoresis.

All real-time PCR reactions were performed in triplicate using a GenAmp® 7300 Sequence Detection System (Applied Biosystems, Foster City, Calif.). First strand cDNAs were synthesized from 2 µg of total RNA in a 100 mL reaction volume using the TaqMan Reverse Transcription Reagents Kit (Applied Biosystems) per manufacturer's instructions. Independent PCR reactions were performed using the same cDNA for both the gene of interest (stilbene synthase or SbOMT3) and 18S rRNA, using the SYBR® Green PCR Master Mix (Applied Biosystems) with the following gene-specific primer pairs: SbOMT3 forward: 5'-CAATTTC-CCTTTTATGTTTAGCCTGATAG-3' (SEQ ID NO:7), reverse: 5'-TGCCAGGGTGTGATATGTGC-3' (SEQ ID NO:8); peanut stilbene synthase forward: 5'-CCTGTGCCA-GAGGTTGAGAAG-3'(SEQ ID NO:27), reverse: 5'-TGC-CAGGGACAAGTTTTTGAT-3'(SEQ ID NO:28); 18S rRNA-forward: 5'-GGCTCGAAGACGATCAGATACC-3' (SEQ ID NO:29), reverse: 5'-TCGGCATCGTTTA TGGTT-3'(SEQ ID NO:30). Primers were designed using Primer Express® software (Applied Biosystems) and the Amplify program (Engels, W. R. supra). A dissociation curve was generated at the end of each PCR cycle to verify that a single product was amplified using software provided with the GeneAmp® 7300 sequence detection system. A negative control reaction in the absence of template (no template control) was also routinely performed in triplicate for each primer pair. The change in fluorescence of SYBR® Green I dye in every cycle was monitored by the GenAmp® 7300 system software, and the threshold cycle (CT) above background for each reaction was calculated. The CT value of 18S rRNA was subtracted from that of the gene of interest to obtain a $\Delta$CT value. The CT value of an arbitrary calibrator (e.g., the tissue sample from which the largest $\Delta$CT values were obtained) was subtracted from the $\Delta$CT value to obtain a $\Delta\Delta$CT value. The fold-changes in expression level relative to the calibrator were expressed as 2-DDCT.

To assess whether pterostilbene was produced in plants harboring pCRO1 (FIG. 9), leaf samples were collected from various transgenic tobacco lines, as described above for real-time PCR assays, and analyzed by gas chromatography/mass spectrometry (GC-MS) as previously described (Rimando et al. 2004. *J Agric Food Chem.* 52:4713-4719). Lyophilized samples were first powdered using a mortar and pestle, then extracted with methanol:acetone:water:acetic acid (40:40:20:0.1) in an accelerated solvent extraction apparatus. The extracts were subsequently concentrated to a small volume, partitioned with ethyl acetate, then dried under vacuum using a rotary evaporator (BUchi Rotovapor, Brinkmann Instruments) at 30° C. An aliquot (1 mg) of the ethyl acetate fraction was derivatized with 100 µL of a mixture of bis (trimethylsilyl)trifluoroacetamide:dimethylformamide (1:1), and analyzed by GC-MS for the presence of pterostilbene using a JEOL GCMate II System (JEOL USA Inc., Peabody, Mass.).

Figure 10:
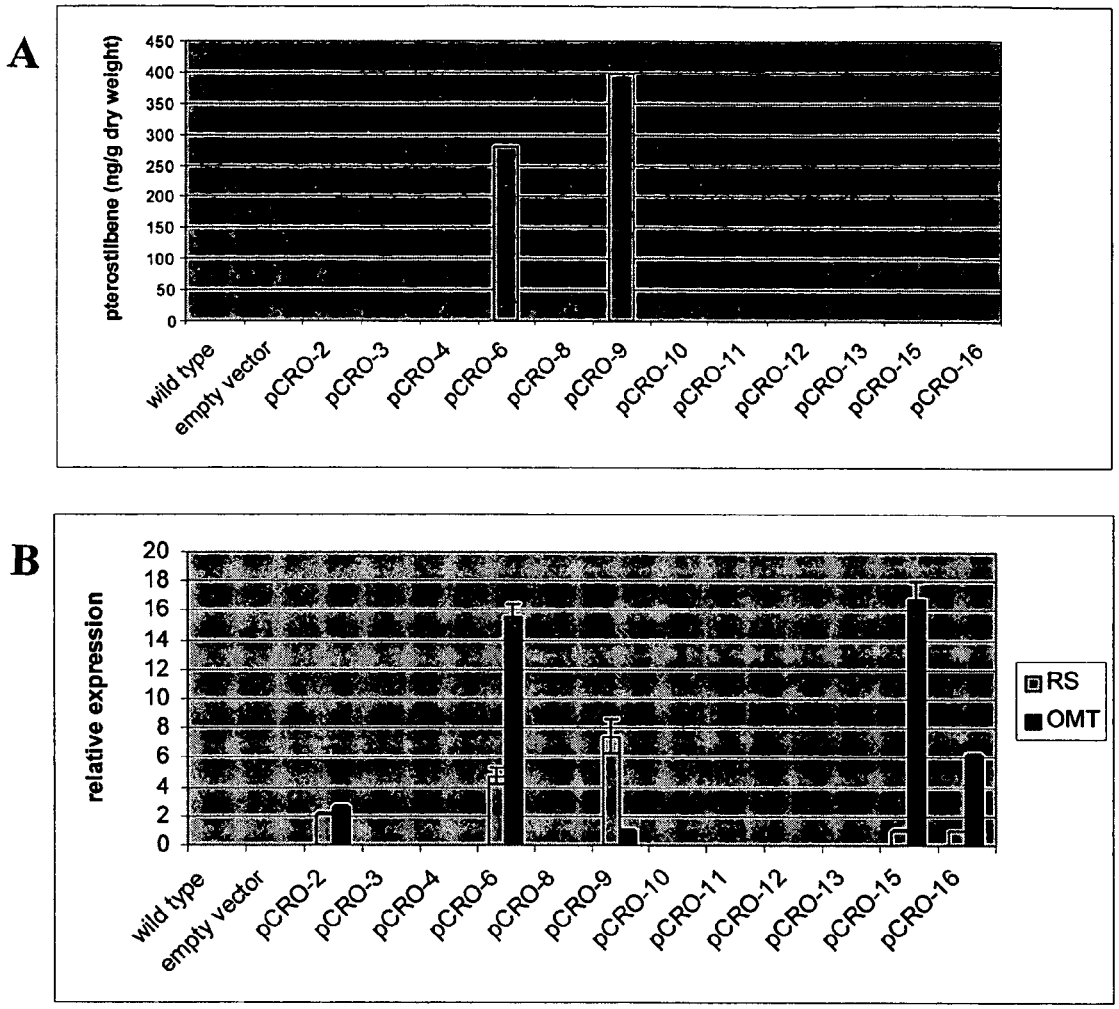
FIGS. 10A and 10B show the relative transgene expression and pterostilbene content in transgenic and wild type *N. tabacum* plants.

The results of both the quantitative real-time PCR gene expression assays and pterostilbene analyses are shown in FIG. 10. A total of 12 independent tobacco lines transformed with the pCRO1 dual-cassette binary vector were screened for the expression of both the 35S::stilbene synthase and 35S::SbOMT3 transcripts, as well as for the presence of pterostilbene. Five out of the 12 lines were found to express the transgenes (FIG. 10); both the 35S::stilbene synthase and 35S::SbOMT3 transcripts were detected in all five of these positive lines. As is typically seen in transformed plant populations, significant variation was observed in transcript accumulation levels among the various transformants, and the levels of the two different transcripts varied somewhat independently. For example, the highest levels of SbOMT3 transcripts were observed in line pCRO-15 (FIG. 10); however, levels of stilbene synthase transcripts in PCRO-15 were significantly lower than the levels observed in lines pCRO-2, pCRO-6, and pCRO-9.

Importantly, significant accumulation of pterostilbene was detected in lines pCRO-6 and pCRO-9, quantified at approximately 280 and 400 ng/gm dry weight, respectively (FIG. 10). pCRO-6 and pCRO-9 also showed the highest 35S::stilbene synthase transcript levels, raising the possibility that stilbene synthase activity levels were not sufficient to support pterostilbene production in the other pCRO1-transformed lines. In wild-type and 'empty vector'-transformed tobacco lines, neither transgene-associated transcripts nor pterostilbene accumulated to detectable levels (FIG. 10).

These experiments demonstrate the utility of the invention described herein: transgenic plants expressing both a stilbene synthase-type enzyme in conjunction with the sorghum O-methyltransferase SbOMT3 accumulate the predicted product pterostilbene. The ability of SbOMT3 to efficiently use resveratrol as a substrate in planta is a central feature of this technology.

The present proof-of-concept represents a relatively simple test case, which can be further optimized for the production of pterostilbene at higher levels or in specific tissues, for example, by the use of alternative promoter elements or other genetic elements required for the optimal expression of the transgene cassettes employed. It is anticipated that these relatively straight-forward modifications would result in significant increases in pterostilbene production, or in the production in specific plant organs such as developing seeds or fruits. Alternative stilbene synthase enzymes could also be employed with more favorable kinetics that could also significantly enhance pterostilbene production.

In addition, while both transgene cassettes in pCRO1 use the strong, constitutively-expressed CaMV 35S promoter (FIG. 9), gene promoters specifically induced by chemicals, pathogen infection, and other types of elicitors could be employed. In this case, pterostilbene would only be produced when crops are treated with specific chemical elicitors by growers, or automatically produced when plants are under attack by microorganisms or other adverse circumstances where pterostilbene production would be beneficial to overall crop yields.

It is likely that SbOMT3 represents a novel subclass of type I plant-specific OMT enzymes, exhibiting a substrate profile that has not previously been demonstrated for any plant OMT to our knowledge. Moreover, phylogenetic analyses of putative and functionally characterized plant-specific type II OMT enzymes indicates that SbOMT3 falls within a distinct Glade of OMTs, which include predicted sequences from rice and corn whose function at the present time remains obscure. The observed preference for alk(en)ylresorcinolic substrates is particularly intriguing with respect to the consideration of a possible role for SbOMT3 in the sorgoleone biosynthetic pathway. The generation of sorgoleones is complex and involves many intermediaries; however, as more information becomes available and additional biosynthetic enzymes become identified, SbOMT3 may additionally be used to increase the accumulation of sorgoleones in the root hairs and roots of sorghum and other food crops to ensure the suppression of weeds and thus higher yields of food crops.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated or recombinant nucleic acid comprising a sequence that encodes a polypeptide having the amino acid sequence set forth in SEQ ID NO:2.

2. An isolated or recombinant nucleic acid comprising a sequence that encodes a polypeptide comprising an amino acid sequence having at least 90% sequence identity to the amino acid sequence set forth in SEQ ID NO:2, wherein the polypeptide has O-methyltransferase activity.

3. An isolated or recombinant nucleic acid comprising a sequence that encodes a polypeptide comprising an amino acid sequence having at least 95% sequence identity to the amino acid sequence set forth in SEQ ID NO:2, wherein the polypeptide has O-methyltransferase activity.

4. An isolated or recombinant nucleic acid comprising a sequence that encodes a polypeptide comprising an amino acid sequence having at least 99% sequence identity to the amino acid sequence set forth in SEQ ID NO:2, wherein the polypeptide has O-methyltransferase activity.

5. An isolated or recombinant nucleic acid comprising the sequence set forth in SEQ ID NO:1.

6. An isolated or recombinant nucleic acid comprising a sequence that encodes a polypeptide having O-methyltransferase activity, said sequence comprising a sequence having at least 90% sequence identity to SEQ ID NO:1, as determined by analysis with a sequence comparison algorithm or by visual inspection, or a sequence fully complementary to said sequence.

7. An isolated or recombinant nucleic acid comprising a sequence that encodes a polypeptide having O-methyltransferase activity, said sequence comprising a sequence having at least 95% sequence identity to SEQ ID NO:1, as determined by analysis with a sequence comparison algorithm or by visual inspection, or a sequence fully complementary to said sequence.

8. An isolated or recombinant nucleic acid comprising a sequence that encodes a polypeptide having O-methyltransferase activity, said sequence comprising a sequence having at least 99% sequence identity to SEQ ID NO:1, as determined by analysis with a sequence comparison algorithm or by visual inspection, or a sequence fully complementary to said sequence.

9. The isolated nucleic acid of any one of claims 1 to 8, further comprising one or more regulatory elements operatively linked to said nucleic acid.

10. The nucleic acid molecule according to claim 1, wherein the nucleotide sequence is optimized for expression in a plant.

11. A DNA construct comprising the nucleic acid molecule of claim 1, wherein said nucleotide sequence is linked to a promoter that drives expression in a host cell.

12. A vector comprising the nucleic acid of claim 1.

13. A host cell comprising the vector of claim 12.

14. The host cell of claim 13, wherein said host cell is a plant cell into which the construct according to the invention can be introduced wherein expression of said construct results in the production of pterostilbene.

15. A transgenic plant containing the nucleic acid sequence according to claim 1 or a progeny of said plant containing the nucleic acid sequence according to claim 1 wherein the level of pterostilbene accumulation in said plant or progeny of said plant is altered when compared to plants of the same species which have not been transformed.

16. A transgenic plant in which the nucleic acid sequence according to claim 1 has been introduced or a progeny of said plant in which said nucleic acid sequence has been introduced and in which the level of pterostilbene accumulation in said plant or progeny of said plant is altered, or a tissue thereof.

17. A plant cell or plant part of the plant of claim 15 or 16.

18. A transgenic plant containing the nucleic acid sequence according to any one of claims 1-8 or a progeny of said plant containing the nucleic acid sequence according to any one of claims 1-8 wherein the level of pterostilbene accumulation in said plant or progeny of said plant is altered when compared to plants of the same species which have not been transformed.

19. The transgenic plant of claim 18 where the plant is a monocotyledonous plant.

20. The transgenic plant of claim 18 where the plant is a dicotyledonous plant.

21. A host cell having stably incorporated into its genome at least one DNA construct of claim 11.

22. The host cell of claim 21, wherein said host cell is a plant cell into which the construct according to the invention can be introduced so as to produce pterostilbene.

23. The host cell of claim 22, wherein the plant cell is from a plant selected from the group consisting of grape, cranberry, blueberry, and medicago.

24. A transformed plant produced by a method comprising: transforming a plant with the nucleic acid of claim 1.

25. A method of increasing pterostilbene in a plant comprising introducing the nucleic acid sequence according to claim 1 into a plant or plant cells and then allowing said nucleic acid sequence to be expressed in said plant or plant cells.

26. A method of increasing pterostilbene content in a plant or plant cell comprising introducing into a plant at least one DNA construct comprising a nucleotide operably linked to a promoter that drives expression in a plant cell, wherein said nucleotide sequence is selected from the group consisting of:
(a) an isolated or recombinant nucleic acid comprising a sequence that encodes a polypeptide having the amino acid sequence set forth in SEQ ID NO:2;
(b) an isolated or recombinant nucleic acid comprising a sequence that encodes a polypeptide comprising an amino acid sequence having at least 90% sequence identity to the amino acid sequence set forth in SEQ ID NO:2, wherein the polypeptide has O-methyltransferase activity;
(c) an isolated or recombinant nucleic acid comprising a sequence that encodes a polypeptide comprising an amino acid sequence having at least 95% sequence identity to the amino acid sequence set forth in SEQ ID NO:2, wherein the polypeptide has O-methyltransferase activity;
(d) an isolated or recombinant nucleic acid comprising a sequence that encodes a polypeptide comprising an amino acid sequence having at least 99% sequence identity to the amino acid sequence set forth in SEQ ID NO:2, wherein the polypeptide has O-methyltransferase activity;
(e) an isolated or recombinant nucleic acid comprising the sequence set forth in SEQ ID NO:1;
(f) an isolated or recombinant nucleic acid comprising a sequence that encodes a polypeptide having O-methyltransferase activity, said sequence comprising a sequence having at least 90% sequence identity to SEQ ID NO:1, as determined by analysis with a sequence comparison algorithm or by visual inspection;
(g) an isolated or recombinant nucleic acid comprising a sequence that encodes a polypeptide having O-methyltransferase activity, said sequence comprising a sequence having at least 95% sequence identity to SEQ ID NO:1, as determined by analysis with a sequence comparison algorithm or by visual inspection;
(h) an isolated or recombinant nucleic acid comprising a sequence that encodes a polypeptide having O-methyltransferase activity, said sequence comprising a sequence having at least 99% sequence identity to SEQ ID NO:1, as determined by analysis with a sequence comparison algorithm or by visual inspection; and
(i) an isolated nucleic acid having the sequence set forth in SEQ ID NO: 1; and then allowing said nucleic acid sequence to be expressed in said plant or plant cell so as to thereby increase the accumulation of pterostilbene in the plant or plant cell.

27. The method for increasing accumulation of pterostilbene in a plant cell according to claim 26 wherein the plant cell is a cell of grape, cranberry, blueberry, and medicago.

28. A method for increasing accumulation of pterostilbene in a plant cell comprising transfecting the cell with the nucleic acid of claim 1 linked to a nucleic acid which is a regulatory sequence enabling expression of the nucleic acid in the cell, so as to thereby increase the accumulation of pterostilbene in the plant cell.

* * * * *

SEQUENCE LISTING

<160> NUMBER OF SEQ ID NOS: 30

<210> SEQ ID NO 1
<211> LENGTH: 1126
<212> TYPE: DNA
<213> ORGANISM: Sorghum bicolor

<400> SEQUENCE: 1

| | | | | | |
|---|---|---|---|---|---|
| atggtactca | tcagcgagga | cagtagggag | ttgctccaag | cccacgtcga | gctatggaac | 60 |
| cagacctaca | gctttatgaa | gtcggtggca | ctcgccgttg | ctttggacct | ccacatcgct | 120 |
| gatgccatcc | accgccgtgg | tggcgccgcc | accctctccc | agatacttgg | agagattggt | 180 |
| gtccgcccat | gtaagcttcc | tggcctccat | cgcataatgc | gcgttctcac | cgtctcagga | 240 |
| accttcacca | tcgtccagcc | atcagcggaa | accatgtcat | cagagtcaga | cgggcgtgag | 300 |
| cctgtctata | agctgacaac | agcgtccagc | ctcctcgtca | gcagcgagag | ctcggcgaca | 360 |
| gcgagcttgt | ctcctatgct | aaaccatgtg | cttagcccct | tccgtgactc | gccgctcagc | 420 |
| atggggctca | ctgcgtggtt | ccggcatgat | gaagatgaac | aggcgcctgg | catgtgcccg | 480 |
| ttcaccttga | tgtacggcac | aaccttgtgg | gaggtgtkca | ggcgcgacga | cgcaatcaac | 540 |
| gcgttgttca | acaatgccat | ggccgcagac | agcaacttcc | tcatgcagat | tctcttgaag | 600 |
| gagttcagcg | aggtcttcct | tgggatagac | tcgctggtcg | acgtcgccgg | cggggttggg | 660 |
| ggagccacca | tggccattgc | ggcggcattt | ccgtgtttga | agtgtaccgt | gctggacctc | 720 |
| cctcacgttg | ttgccaaggc | tccttctagt | tctattggca | acgtgcagtt | tgttgggggt | 780 |
| gacatgtttg | agagcattcc | accagcaaat | gttgtcctcc | tcaagtggat | tttacatgac | 840 |
| tggagcaatg | atgagtgtat | caagatattg | aagaattgca | agcaagctat | cccttctaga | 900 |
| gatgcaggag | gaaagataat | aatcattgat | gttgtggttg | ggtctgattc | atcagacacc | 960 |
| aagcttctgg | agacgcaagt | aatctatgat | ctccatctca | tgaaaattgg | tggggttgaa | 1020 |
| cgagatgagc | aagagtggaa | gaaaatattc | ctcgaagctg | gatttaagga | ctacaagatt | 1080 |
| atgccgattt | taggcctccg | atcgatcatt | gagctatatc | catgag | | 1126 |

<210> SEQ ID NO 2
<211> LENGTH: 375
<212> TYPE: PRT
<213> ORGANISM: Sorghum bicolor

<400> SEQUENCE: 2

Met Val Leu Ile Ser Glu Asp Ser Arg Glu Leu Leu Gln Ala His Val
1               5                   10                  15

Glu Leu Trp Asn Gln Thr Tyr Ser Phe Met Lys Ser Val Ala Leu Ala
            20                  25                  30

Val Ala Leu Asp Leu His Ile Ala Asp Ala Ile His Arg Arg Gly Gly
        35                  40                  45

Ala Ala Thr Leu Ser Gln Ile Leu Gly Glu Ile Gly Val Arg Pro Cys
    50                  55                  60

Lys Leu Pro Gly Leu His Arg Ile Met Arg Val Leu Thr Val Ser Gly
65                  70                  75                  80

```
Thr Phe Thr Ile Val Gln Pro Ser Ala Glu Thr Met Ser Ser Glu Ser
                85                  90                  95

Asp Gly Arg Glu Pro Val Tyr Lys Leu Thr Thr Ala Ser Ser Leu Leu
            100                 105                 110

Val Ser Ser Glu Ser Ser Ala Thr Ala Ser Leu Ser Pro Met Leu Asn
        115                 120                 125

His Val Leu Ser Pro Phe Arg Asp Ser Pro Leu Ser Met Gly Leu Thr
    130                 135                 140

Ala Trp Phe Arg His Asp Glu Asp Gln Ala Pro Gly Met Cys Pro
145                 150                 155                 160

Phe Thr Leu Met Tyr Gly Thr Thr Leu Trp Glu Val Cys Arg Arg Asp
                165                 170                 175

Asp Ala Ile Asn Ala Leu Phe Asn Asn Ala Met Ala Ala Asp Ser Asn
            180                 185                 190

Phe Leu Met Gln Ile Leu Leu Lys Glu Phe Ser Glu Val Phe Leu Gly
        195                 200                 205

Ile Asp Ser Leu Val Asp Val Ala Gly Gly Val Gly Gly Ala Thr Met
    210                 215                 220

Ala Ile Ala Ala Ala Phe Pro Cys Leu Lys Cys Thr Val Leu Asp Leu
225                 230                 235                 240

Pro His Val Val Ala Lys Ala Pro Ser Ser Ile Gly Asn Val Gln
                245                 250                 255

Phe Val Gly Gly Asp Met Phe Glu Ser Ile Pro Pro Ala Asn Val Val
            260                 265                 270

Leu Leu Lys Trp Ile Leu His Asp Trp Ser Asn Asp Glu Cys Ile Lys
        275                 280                 285

Ile Leu Lys Asn Cys Lys Gln Ala Ala Ile Pro Ser Arg Asp Ala Gly
    290                 295                 300

Gly Lys Ile Ile Ile Ile Asp Val Val Val Gly Ser Asp Ser Ser Asp
305                 310                 315                 320

Thr Lys Leu Leu Glu Thr Gln Val Ile Tyr Asp Leu His Leu Met Lys
                325                 330                 335

Ile Gly Gly Val Glu Arg Asp Glu Gln Glu Trp Lys Lys Ile Phe Leu
            340                 345                 350

Glu Ala Gly Phe Lys Asp Tyr Lys Ile Met Pro Ile Leu Gly Leu Arg
        355                 360                 365

Ser Ile Ile Glu Leu Tyr Pro
    370                 375

<210> SEQ ID NO 3
<211> LENGTH: 27
<212> TYPE: DNA
<213> ORGANISM: Sorghum bicolor

<400> SEQUENCE: 3
gcatcttcgt tcatgtactt gttacac                                      27

<210> SEQ ID NO 4
<211> LENGTH: 25
<212> TYPE: DNA
<213> ORGANISM: Sorghum bicolor

<400> SEQUENCE: 4
cgacgaagca catccttact atgag                                        25

<210> SEQ ID NO 5
```

```
<211> LENGTH: 16
<212> TYPE: DNA
<213> ORGANISM: Sorghum bicolor

<400> SEQUENCE: 5
cctcgttttc gtatgc                                                       16

<210> SEQ ID NO 6
<211> LENGTH: 3
<212> TYPE: DNA
<213> ORGANISM: Sorghum bicolor

<400> SEQUENCE: 6 tgc                                                                      3

<210> SEQ ID NO 7
<211> LENGTH: 3
<212> TYPE: DNA
<213> ORGANISM: Sorghum bicolor

<400> SEQUENCE: 7 tag                                                                      3

<210> SEQ ID NO 8
<211> LENGTH: 20
<212> TYPE: DNA
<213> ORGANISM: Sorghum bicolor

<400> SEQUENCE: 8
tgccagggtg tgatatgtgc                                                   20

<210> SEQ ID NO 9
<211> LENGTH: 23
<212> TYPE: DNA
<213> ORGANISM: Sorghum bicolor

<400> SEQUENCE: 9
cttcctctgt ccctctgatg gag                                               23

<210> SEQ ID NO 10
<211> LENGTH: 20
<212> TYPE: DNA
<213> ORGANISM: Sorghum bicolor

<400> SEQUENCE: 10
aagacacgac cacgacatgc                                                   20

<210> SEQ ID NO 11
<211> LENGTH: 21
<212> TYPE: DNA
<213> ORGANISM: Sorghum bicolor

<400> SEQUENCE: 11
tggattgatt gatgctgcaa g                                                 21

<210> SEQ ID NO 12
<211> LENGTH: 23
<212> TYPE: DNA
<213> ORGANISM: Sorghum bicolor

<400> SEQUENCE: 12
cgtgaaacaa gagacacaca tgc                                               23
```

```
<210> SEQ ID NO 13
<211> LENGTH: 22
<212> TYPE: DNA
<213> ORGANISM: Sorghum bicolor

<400> SEQUENCE: 13
ggctcgaaga cgatcagata cc                                             22

<210> SEQ ID NO 14
<211> LENGTH: 4
<212> TYPE: DNA
<213> ORGANISM: Sorghum bicolor

<400> SEQUENCE: 14 ggtt                                                                  4

<210> SEQ ID NO 15
<211> LENGTH: 23
<212> TYPE: DNA
<213> ORGANISM: Sorghum bicolor

<400> SEQUENCE: 15
caccagaaga aacactagca tcg                                            23

<210> SEQ ID NO 16
<211> LENGTH: 27
<212> TYPE: DNA
<213> ORGANISM: Sorghum bicolor

<400> SEQUENCE: 16
ttaaggacca ataagcaagc tagtaca                                        27

<210> SEQ ID NO 17
<211> LENGTH: 19
<212> TYPE: DNA
<213> ORGANISM: Sorghum bicolor

<400> SEQUENCE: 17
gaagcacagc tgctgatgg                                                 19

<210> SEQ ID NO 18
<211> LENGTH: 25
<212> TYPE: DNA
<213> ORGANISM: Sorghum bicolor

<400> SEQUENCE: 18
cagcaagcaa cacacatcaa gtatg                                          25

<210> SEQ ID NO 19
<211> LENGTH: 22
<212> TYPE: DNA
<213> ORGANISM: Sorghum bicolor

<400> SEQUENCE: 19
atgactggag caatgatgag tg                                             22

<210> SEQ ID NO 20
<211> LENGTH: 4
<212> TYPE: DNA
<213> ORGANISM: Sorghum bicolor

<400> SEQUENCE: 20 tgtg                                                                  4
```

```
<210> SEQ ID NO 21
<211> LENGTH: 19
<212> TYPE: DNA
<213> ORGANISM: Sorghum bicolor

<400> SEQUENCE: 21
gctatactag tactagtgg                                            19

<210> SEQ ID NO 22
<211> LENGTH: 15
<212> TYPE: DNA
<213> ORGANISM: Sorghum bicolor

<400> SEQUENCE: 22
ttgtgaattc atggg                                                15

<210> SEQ ID NO 23
<211> LENGTH: 16
<212> TYPE: DNA
<213> ORGANISM: Sorghum bicolor

<400> SEQUENCE: 23
ccgcgtcttc tcatgc                                               16

<210> SEQ ID NO 24
<211> LENGTH: 18
<212> TYPE: DNA
<213> ORGANISM: Sorghum bicolor

<400> SEQUENCE: 24
agacttcgat gacaccac                                             18

<210> SEQ ID NO 25
<211> LENGTH: 23
<212> TYPE: DNA
<213> ORGANISM: Sorghum bicolor

<400> SEQUENCE: 25
atatggtact catcagcgag gac                                       23

<210> SEQ ID NO 26
<211> LENGTH: 23
<212> TYPE: DNA
<213> ORGANISM: Sorghum bicolor

<400> SEQUENCE: 26
tcatggatat agctcaatga tcg                                       23

<210> SEQ ID NO 27
<211> LENGTH: 21
<212> TYPE: DNA
<213> ORGANISM: Sorghum bicolor

<400> SEQUENCE: 27
cctgtgccag aggttgagaa g                                         21

<210> SEQ ID NO 28
<211> LENGTH: 21
<212> TYPE: DNA
<213> ORGANISM: Sorghum bicolor

<400> SEQUENCE: 28
tgccagggac aagttttga t                                          21
```

```
<210> SEQ ID NO 29
<211> LENGTH: 22
<212> TYPE: DNA
<213> ORGANISM: Sorghum bicolor

<400> SEQUENCE: 29
ggctcgaaga cgatcagata cc                                                  22

<210> SEQ ID NO 30
<211> LENGTH: 5
<212> TYPE: DNA
<213> ORGANISM: Sorghum bicolor

<400> SEQUENCE: 30 tggtt                                                                      5
```